United States Patent
Bandow et al.

(10) Patent No.: US 11,866,757 B2
(45) Date of Patent: Jan. 9, 2024

(54) PLASMA-DRIVEN BIOCATALYSIS

(71) Applicant: Ruhr-Universitaet Bochum, Bochum (DE)

(72) Inventors: Julia Bandow, Witten (DE); Abdulkadir Yayci, Bochum (DE); Marco Krewing, Hamburg (DE); Robert Kourist, Graz (AT); Alvaro Gomez Baraibar, Bochum (DE)

(73) Assignee: Ruhr-Universitaet Bochum, Bochum (DE)

(*) Notice: Subject to any disclaimer, the term of this patent is extended or adjusted under 35 U.S.C. 154(b) by 0 days.

(21) Appl. No.: 17/254,929

(22) PCT Filed: Jun. 11, 2019

(86) PCT No.: PCT/EP2019/065220
§ 371 (c)(1),
(2) Date: Dec. 22, 2020

(87) PCT Pub. No.: WO2020/007576
PCT Pub. Date: Jan. 9, 2020

(65) Prior Publication Data
US 2021/0115479 A1 Apr. 22, 2021

(30) Foreign Application Priority Data

Jul. 3, 2018 (DE) .................... 10 2018 116 052.6

(51) Int. Cl.
C12P 7/22 (2006.01)
C12N 9/04 (2006.01)
C12N 9/08 (2006.01)
C12N 9/02 (2006.01)

(52) U.S. Cl.
CPC .............. *C12P 7/22* (2013.01); *C12N 9/0006* (2013.01); *C12N 9/0065* (2013.01); *C12N 9/0069* (2013.01)

(58) Field of Classification Search
None
See application file for complete search history.

(56) References Cited

U.S. PATENT DOCUMENTS

2008/0006536 A1  1/2008  Cuomo et al.
2010/0279366 A1  11/2010  Pecyna et al.

FOREIGN PATENT DOCUMENTS

CA        2379518 A1       2/2001
DE  102007016139 A1      10/2008
WO     2011120938 A2     10/2011

OTHER PUBLICATIONS

Sears et al., Measurement of hydrogen peroxide concentrations in plasma activated media, 22nd International Symposium on Plasma Chemistry, 2015. (Year: 2015).*
Molina-Espeja et al., Directed Evolution of Unspecific Peroxygenase from Agrocybe aegerita, Applied Env. Microbiol. 80, 2014, 3496-3507. (Year: 2014).*
Bormann et al., Specific oxyfunctionalisations catalyzed by peroxygenases, Catalysis Sci. Technol. 5, 2015, 2038. (Year: 2015).*
Zhang et al., Effects and Mechanism of Atmospheric-Pressure Dielectric Barrier Discharge Cold Plasma on Lactate Dehydrogenase (LDH) Enzyme, Sci. Reports 5, 2015, 10031. (Year: 2015).*
Hofrichter et al., Oxidations catalyzed by fungal peroxygenases, Curr. Opin. Chem. Biol. 19, 2014, 116-25. (Year: 2014).*
Li et al., Manipulation of Lipase Activity by the Helium Radio-Frequency, Plasma Process. Polym. 8, 2011, 224-229. (Year: 2011).*
Yayci et al., Plasma-Driven in Situ Production of Hydrogen Peroxide for Biocatalysis, ChemSusChem 13, 2020, 2072-79. (Year: 2020).*
Yushkova (Synthesis of Spin-Labeled Amides of 6-Hydroxy-2,5,7,8-Tetramethylchroman-2-Carboxylic Acid (TROLOX), Chem. Nat. Compounds 49, 2013, 253. (Year: 2013).*
Hofrichter et al., "Oxidations catalyzed by fungal peroxygenases", Current Opinion in Chemical Biology, 2014, pp. 116-125, vol. 19, Elsevier Ltd.
Bormann et al., "Specific oxyfunctionalisations catalysed by peroxygenases: opportunities, challenges and solutions", Catalysis Science & Technology, 2015, pp. 2038-2052, vol. 5, The Royal Society of Chemistry.
Horst et al., "Electro-enzymatic hydroxylation of ethylbenzene by the evolved unspecific peroxygenase of Agrocybe aegerita", Journal of Molecular Catalysis B: Enzymatic, 2016, pp. 137-142, vol. 133, Elsevier B.V.
Zachos et al., "Photobiocatalytic decarboxylation for olefin synthesis", Chemical Communications, 2015, pp. 1918-1921, vol. 51, The Royal Society of Chemistry.
Benedikt et al., "The fate of plasma-generated oxygen atoms in aqueous solutions: non-equilibrium atmospheric pressure plasmas as an efficient source of atomic O(aq)", Physical Chemistry Chemical Physics, 2018, pp. 12037-12042, vol. 20, The Royal Society of Chemistry.
Pankaj et al., "Kinetics of tomato peroxidase inactivation by atmospheric pressure cold plasma based on dielectric barrier discharge", Innovative Food Science & Emerging Technologies, 2013, pp. 153-157, vol. 19, Elsevier B.V.
International search report from parallel PCT Patent Application PCT/EP2019/065220 dated Sep. 17, 2019, 20 pages (for reference purposes only).

* cited by examiner

Primary Examiner — Todd M Epstein
(74) Attorney, Agent, or Firm — VIERING JENTSCHURA & PARTNER MBB

(57) ABSTRACT

Methods using plasma-driven generation of $H_2O_2$ in an aqueous liquid may provide a substrate to enzymes, which are then capable to oxidize or hydroxylate organic compounds. A plasma device may produce an aqueous liquid comprising $H_2O_2$ for use in an enzymatic reaction.

11 Claims, 13 Drawing Sheets

PLASMA-DRIVEN BIOCATALYSIS

CROSS-REFERENCE TO RELATED APPLICATIONS

The present application is a national stage entry according to 35 U.S.C. § 371 of PCT application No.: PCT/EP2019/065220 filed on Jun. 11, 2019; which claims priority to German Patent Application Serial No.: 10 2018 116 052.6.0 filed on Jul. 3, 2018; all of which are incorporated herein by reference in their entirety and for all purposes.

TECHNICAL FIELD

The present invention relates to methods using plasma-driven generation of $H_2O_2$ in an aqueous liquid to provide this substrate to enzymes, which are thereby capable to oxidize or hydroxylate organic compounds. The invention further relates to the use of a plasma device for producing aqueous liquid comprising $H_2O_2$ for use in an enzymatic reaction.

BACKGROUND

Peroxidases catalyze the reduction of $H_2O_2$ and the oxidation of a substrate, mostly by employing a heme cofactor. In vivo, they act in the condensation of biopolymers, in the field of immune defense, or in the detoxification of reactive $H_2O_2$. Furthermore, they are valuable enzymes for biocatalysis, because of their stability under operating conditions and their broad product range. Peroxygenases are valuable biocatalysts, as well, since they use $H_2O_2$ through the so called "peroxide shunt pathway", eliminating the need for expensive electron donors, such as flavins or nicotinamide cofactors (Hofrichter et al., Curr. Opin. Chem. Biol., 2014, 19, 116-125; Bormann et al., Catal. Sci. Technol., 2015, 5, 2038-2052). However, the industrial application of peroxidases or peroxygenases is limited due to their partial or complete inactivation in the presence of higher concentrations of peroxides.

Since the addition of $H_2O_2$ in low concentrations to the reaction mixture is technically difficult to realize, it was proposed to alternatively produce $H_2O_2$ in situ. One way is the utilization of enzymes or enzyme cascades. In this case, further enzymes and cofactors would be needed. This makes this approach more expensive and complex, even for small scale applications, which is not desired.

Furthermore, it was proposed to produce $H_2O_2$ electrochemically in substantial concentrations (Horst et al., J. Mol. Catal. B: Enzym., 2016, 133, 137-142). However, this approach is less efficient, since the enzymes and buffer salts may precipitate at immersed electrodes.

In addition, a light-driven in situ $H_2O_2$-generation system is known, for example for the selective and quantitative conversion of fatty acids into terminal alkenes (Zachos et al., Chem. Commun., 2015, 51, 1918-1921). Current light-driven systems either rely on an organic electron donor or catalytic water oxidation as electron source. The stoichiometric supply of electron donors such as ethylenediamine tetraacetic acid (EDTA) suffers from a poor atom economy. The degradation of the electron donor creates side products. The separation of the desired reaction product from side-products requires additional effort. Catalytic water oxidation produces reactive oxygen species throughout the reaction volume that decrease the stability of enzymes, which is an inherent disadvantage. Accumulation of EDTA decomposition products can affect the enzymatic catalysis and need to be removed by additional downstream processing.

As stated above, many strategies are known to produce $H_2O_2$ in situ, however, all of these known methods are either inefficient or require the addition of extra components to the reaction, making them less efficient and more expensive.

SUMMARY

The inventors thus had the objective to provide a less complex method, which is suitable to be employed in medium sized or industrial scales and can preferably be run in an automated process.

Surprisingly, the inventors found that the above-stated drawbacks can be overcome by one of the following methods:

In a first aspect, a method of enzymatically oxidizing or hydroxylating an organic compound may include
i) treating an aqueous liquid comprising at least one enzyme, at least one organic compound, and optionally at least one solvent, which is not water, with a plasma device to obtain an aqueous liquid comprising $H_2O_2$, thereby forming an enzymatically oxidized or hydroxylated organic compound; and
ii) optionally extracting the aqueous liquid obtained after step i) to isolate the oxidized or hydroxylated organic compound.

In a second aspect, a method of enzymatically oxidizing or hydroxylating an organic compound, may include:
i) treating an aqueous liquid with a plasma device to obtain an aqueous liquid comprising $H_2O_2$;
ii) allowing the obtained liquid from step i) to rest for 1 second to 30 minutes, preferably 1 minute to 20 minutes, more preferably 5 minutes to 15 minutes; iii) subsequently adding at least one enzyme, and optionally at least one solvent, which is not water, to the aqueous liquid of step ii);
iv) incubating the mixture obtained in step iii) in order to obtain the enzymatically oxidized or hydroxylated organic compound;
v) optionally extracting the mixture obtained in step iv) to isolate the oxidized or hydroxylated organic compound;
wherein the at least one organic compound is added in step i) or step iii).

Furthermore, in a third aspect, a plasma device, preferably an atmospheric pressure plasma device, more preferably a dielectric barrier discharge device, for producing aqueous liquid comprising $H_2O_2$ may be for use in an enzymatic reaction.

"At least one", as used herein, means one or more, i.e. 1, 2, 3, 4, 5, 6, 7, 8, 9 or more of the referenced species. Similarly, "one or more", as used herein, relates to at least one and comprises 1, 2, 3, 4, 5, 6, 7, 8, 9 or more. In connection with a given species, the term does not relate to the total number of molecules, but rather to the type of species. "At least one enzyme", for example, thus means that one type of enzyme or two or more different types of enzymes may be present. In connection with amounts, the term relates to the total amount of the referenced species. In case of the enzymes, for example, this means that the given amount is the total amount of all enzymes in the aqueous liquid.

Numeric values specified without decimal places here refer to the full value specified with one decimal place, i.e. for example, 99% means 99.0%, unless otherwise defined.

Concentration values are preferably given in M and mM, respectively, what is consistent with the units mol/L or mmol/L, unless otherwise defined.

The terms "about" or "approximately", in connection with a numerical value, refer to a variance of ±10% with respect to the given numerical value.

The feature "organic compounds" refers to organic compounds, which can be oxidized or hydroxylated by an enzyme.

The at least one enzyme can be added to the aqueous liquid in solid form, preferably immobilized on a solid support, as an aqueous solution or in a buffer solution suitable to stabilized the at least one enzyme.

If a compound is described to be substituted, the substituents are generally known to the skilled person. Preferred substituents are selected from —F, —Cl, —Br, —I, —OH, =O, —$OR^1$, —$NH_2$,
—$NHR^1$, —$NR^{12}$, and —$COOR^1$, wherein $R^1$ is an alkyl group having 1 to 20 carbon atoms.

The following abbreviations are used:
horseradish peroxidase (HRP), unspecific peroxygenase (UPO), chloroperoxidase (CPO), DyP-type peroxidase from Streptomyces chartreusis variant 1 (ScDYP1), DyP-type peroxidase from Streptomyces chartreusis variant 2 (ScDYP2), superoxide dismutase A (SOD), pyrogallol (PG), guaiacol (GC), tetraguaiacol (tGC), ethylbenzene (ETBE), R-1-phenylethanol (1-PhOl) dielectric barrier discharge (DBD), gas chromatography (GC), reactive oxygen species (ROS), reactive nitrogen species (RNS), 2,2'-azino-bis(3-ethylbenzothiazoline-6-sulphonic acid (ABTS), potassium phosphate buffer (KPi buffer), tris(hydroxymethyl)aminomethane buffer (TRIS buffer), 2-[4-(2-hydroxyethyl) piperazin-1-yl]ethanesulfonic acid buffer (HEPES buffer), 2-(N-morpholino)ethanesulfonic acid buffer (MES buffer).

Embodiments, features, and advantages become apparent to the person skilled in the following detailed description and claims. Each feature from one embodiment can be used in any other embodiment. Furthermore, the examples contained herein are intended to describe and illustrate the invention, but do not restrict it. In particular, the invention is not limited to these examples.

All methods treat the aqueous liquid with a plasma device in order to obtain an aqueous liquid comprising $H_2O_2$. Such an approach has not been disclosed in the prior art for enzyme catalyzed reactions.

According to the first aspect (referred to as item 1 as well), the aqueous liquid comprises at least one enzyme and at least one organic compound. The reaction mixture is treated with a plasma device to obtain an aqueous liquid comprising $H_2O_2$, thereby forming an enzymatically oxidized or hydroxylated organic compound.

In this approach, the aqueous liquid comprising the at least one enzyme and the at least one organic compound is preferably directly exposed to the formed plasma of the plasma device and the at least one enzyme can directly convert the generated $H_2O_2$ to produce oxidized or hydroxylated organic compounds.

In a preferred embodiment according to item 1, the operation of the plasma device is interrupted periodically, preferably with periods lasting 1 millisecond to 10 minutes, more preferably 1 second to 1 minute, wherein in each period the plasma is operated preferably for 1 millisecond to 10 minutes and plasma operation paused preferably for the remaining 1 millisecond to 10 minutes. Preferably, this procedure allows to control the concentration of generated $H_2O_2$ and/or reactive oxygen species and/or reactive nitrogen species in the reaction mixture.

The method according to item 1 can be performed in a batch, fed-batch, or continuous process, e.g. in a flow-chemistry process, or in any kind of process that is known to the skilled person. It is preferred that the process is a continuous process.

According to the second aspect (referred to as item 3 as well), a step-wise method of enzymatically oxidizing or hydroxylating an organic compound, comprising or consisting of the steps:
i) treating an aqueous liquid with a plasma device to obtain an aqueous liquid comprising $H_2O_2$;
ii) allowing the obtained liquid from step i) to rest for 1 second to 30 minutes, preferably 1 minute to 20 minutes, more preferably 5 minutes to 15 minutes;
iii) subsequently adding at least one enzyme, and optionally at least one solvent, which is different from the aqueous liquid, to the aqueous liquid of step ii);
iv) incubating the mixture obtained in step iii) in order to obtain the enzymatically oxidized or hydroxylated organic compound;
v) optionally extracting the mixture obtained in step iv) to isolate the oxidized or hydroxylated organic compound;
wherein the at least one organic compound is added in step i) or step iii); is disclosed.

Not to be bound by any theory, it is assumed that during the resting time of step ii) some of the generated reactive oxygen species are reacting or recombining to form $H_2O_2$. This has a positive effect on the stability and activity of the enzyme in the aqueous liquid and increases the $H_2O_2$ concentration in the aqueous liquid.

The method according to item 3 can be performed in a batch, fed-batch, or continuous process, e.g. in a flow-chemistry process, or in any kind of process that is known to the skilled person. It is preferred that the process is a continuous process.

The feature "allowing to rest" in step ii) means that in the defined period the at least one enzyme, and preferably any further components/compounds different from the organic compound to be oxidized or hydroxylated, is/are not added to the liquid obtained after step i). The liquid of step ii) can be unmoved or moved in the defined period. For example the liquid can be transported from one reaction vessel to another reaction vessel or in particular in a continuous process. The movement can preferably be carried out via pumping the liquid through pipes from one reaction vessel to another reaction vessel or in a continuous process.

In a preferred embodiment, in step iii) of the method according to item 3, the at least one organic compound is added to the aqueous liquid subsequently or jointly with the at least one enzyme.

In another preferred embodiment, in step i) of the method according to item 3, the aqueous liquid, comprising the at least one organic compound, is treated with a plasma device to obtain an aqueous liquid comprising at least one organic compound and $H_2O_2$.

In a preferred embodiment according to item 3, a sample of aqueous liquid comprising at least one organic compound, is taken from the reaction mixture, a part of aqueous liquid is treated with plasma, and subsequently is returned to the reaction mixture. Preferably, this step can be performed several times.

In a further preferred embodiment, the enzyme is positioned distant to the surface of the aqueous liquid, which is in proximity to the plasma device, preferably the distance between the surface of the aqueous liquid and the plasma device, more preferably between the surface of the aqueous liquid and the electrode of the plasma device, is 0.1 to 10 mm, preferably 0.5 to 5 mm, most preferably 2 mm.

Furthermore, the enzyme is preferably immobilized, wherein the immobilized enzyme is located between 1 mm and 20 cm from the surface of the aqueous liquid, preferably at the bottom of a reaction chamber or vessel containing the aqueous liquid in which the aqueous liquid is treated, or a reaction channel or tube through which the aqueous liquid is flowing during treatment. The enzyme can be immobilized on a solid support, preferably the enzyme is covalently linked to the solid support or embedded in a polymeric structure, more preferably the enzyme is immobilized by covalent attachment to EC-HA Sepabeads or Relizyme HA403 M beads using glutaraldehyde as linker. Relizyme HA403 M beads are commercially available from Resindion, Binasco, Italy.

A suitable solid support and a suitable immobilization method is, for example, described in Bayraktar et al., International Journal of Biological Macromolecules, 2011, 49, 855. Investigation of unspecific peroxygenase immobilization is, for example, described in Molina-Espeja et al., International journal of molecular sciences, 2019, 20.

Immobilization of enzymes increases their stability in methods. Thus, the immobilization of enzymes allows the use of these enzymes more than 1 time in a method, i.e. the immobilised enzymes can be recycled. In a preferred embodiment, the immobilized enzyme is used 1 time, preferably 2 times, more preferably 3 times, more preferably 4 times, more preferably 5 times, more preferably 6 times, more preferably 7 times and more preferably 8 times in a method.

Preferably, the aqueous liquid in the reaction chamber or vessel is a static liquid during removal and/or addition of aqueous liquid samples. In a non-limiting embodiment, static liquid means that the aqueous liquid in the reaction chamber is preferably not exposed to an active mixing or stronger movement, during removal and/or addition of aqueous liquid samples. In embodiments, in which the aqueous liquid is directly treated with the plasma device in the reaction chamber, a slight movement or mixing of the aqueous liquid can be caused by the treatment with the plasma device, which fulfils the requirements of a static liquid. Preferably, the aqueous solution is not exposed to active mixing during removal and/or addition of aqueous liquid samples, e.g. by a magnetic mixer or any other mixing device.

By using a distance between the enzyme and the surface of the aqueous liquid that is exposed to the plasma, an improved method can be obtained, since the concentration of highly reactive, short-lived, enzyme-toxic species declines in a distance-dependent manner.

In a preferred embodiment, the aqueous liquid is water or an aqueous buffer, more preferably the liquid is an aqueous buffer selected from a phosphate buffer, a tris(hydroxymethyl)aminomethane buffer, a 2-(N-morpholino)ethanesulfonic acid buffer, and a 2-[4-(2-hydroxyethyl)piperazin-1-yl]ethanesulfonic acid buffer.

In a further preferred embodiment the aqueous buffer has a pH value of 4 to 8, preferably 4 to 7, more preferably 5.5, 6 or 7.

By employing an aqueous buffer, the pH can be kept stable, which reduces side reactions of the organic compounds. Furthermore, aqueous buffers can also stabilize the enzyme.

In a further preferred embodiment, the organic compound is selected from unsubstituted or substituted alkanes, alkenes, alkynes, cyclic or aromatic hydrocarbons, heterocyclic hydrocarbons, amino acids, proteins, alkaloids, steroids, and terpenes, or mixtures thereof, more preferably alkyl benzenes, more preferably from ethylbenzene, pyrogallol, or guaiacol, most preferably from ethylbenzene or guaiacol.

In a further preferred embodiment, the at least one enzyme is selected from oxidases, monooxygenases, peroxidases, and peroxygenases, more preferably from unspecific peroxygenase, vanadium chloroperoxidase, DyP-type peroxidase from *Streptomyces chartreusis* variant 1, DyP-type peroxidase from *Streptomyces chartreusis* variant 2, unknown peroxidase and horseradish peroxidase, most preferably from unspecific peroxygenase and horseradish peroxidase.

A preferred enzyme is the UPO from the fungus Agrocybe aegerita. This enzyme combines peroxidase and P450 characteristics, whereby it is able to oxidize or hydroxylate arylbenzenes, aryl alcohols, and aldehydes using $H_2O_2$. By employing this enzyme high turnover numbers, exceeding 10,000 can be reached.

A further preferred enzyme is HRP. HRP can be applied for a wide range of selective reactions, including the synthesis of enantiomerically enriched hydroperoxides and alcohols (Hoch et al., 1997, J. Mol. Catal. A: Chem., 117, 321-328).

Furthermore, chloroperoxidase (CPO) from Caldariomyces fumago are preferred as well. CPO can be applied for a wide range of selective reactions, including the enantioselective oxidation of racemic alcohols (Kiljunen et al., 1999, Tetrahedron: Asymmetry, 10, 3529-3535).

Further preferred enzymes are vanadium chloroperoxidase, DyP-type peroxidase from *Streptomyces chartreusis* variant 1, DyP-type peroxidase from *Streptomyces chartreusis* variant 2 and unknown peroxidase.

In a further preferred embodiment, the enzyme is a modified enzyme, which has a high resistance to reactive compounds, e.g., to $H_2O_2$, more preferably the enzyme is modified by gene mutation of the corresponding gene sequence.

Preferably, modification of an enzyme is related to gene mutation of the corresponding gene sequence, e.g., by substitution, deletion, or insertion of one or more bases within the gene sequence, which encodes for the amino acid sequence of the desired enzyme. Inter alia, site-saturated mutagenesis as well as random mutagenesis, e.g., by UV irradiation, but also any other suitable mutagenesis method, which is known to the skilled person, can be used to introduce gene mutations.

Preferably, the modification of the enzyme results in a higher resistance to reactive compounds, e.g., to $H_2O_2$, than the unmodified wild-type enzyme. Higher resistance means for example, that the modified enzyme tolerates higher $H_2O_2$ concentrations in comparison to the wild-type enzyme.

The genes corresponding to wild-type or modified enzymes can be expressed in bacteria, yeast, baculovirus, tissue culture, and the like. Preferably, the UPO from the fungus Agrocybe aegerita is expressed in the yeast *Pichia pastoris*, bacterial enzymes in *Escherichia coli* or *Bacillus subtilis*. Enzymes can be extracted from natural producers, preferably HRP is extracted from horseradish roots.

In a further preferred embodiment, the aqueous liquid or the obtained aqueous liquid further comprise at least one auxiliary substance, which is selected from scavengers of reactive species, stress response proteins or proteins, in particular detoxifying proteins like superoxide dismutase, protein-protective proteins like molecular chaperones, compounds shielding the enzymes against the enzyme-toxic reactive species, in particular neutral species like excited species and radicals, or charged species like electrons and ions, preferably peroxynitrite, HOCl, nitric acid, singlet oxygen, hydroxyl radicals, atomic oxygen, nitric oxide, superoxide, free electrons.

For example, detoxifying enzymes, such as the superoxide dismutase A (SOD) from *Escherichia coli*, can be used to further increase the peroxide production by conversion of plasma-generated superoxide to $H_2O_2$.

Further suitable detoxifying compounds could be mannitol, TROLOX (6-hydroxy-2,5,7,8-tetramethylchroman-2-carboxylic acid) or Ebselen, uric acid. However, SOD is preferred.

Optionally, the aqueous liquid comprises at least one solvent, which is not water, preferably an organic solvent. In preferred embodiments, the organic solvent is dimethyl sulfoxide.

In a non-limiting embodiment, the aqueous liquid is treated with a plasma device to obtain an aqueous liquid comprising $H_2O_2$. The plasma device generates plasma, more preferably non-thermal or non-equilibrium plasma, which interacts with the aqueous liquid to generate $H_2O_2$.

Plasma parameters, such as frequency, voltage, and power density, can influence the $H_2O_2$ production and can be adjusted to the needs of the enzyme employed.

Preferably, non-equilibrium atmospheric pressure plasma is used, preferably at ambient temperature to treat the aqueous liquid. This allows mild reaction conditions without additional precautions.

In one preferred embodiment, the plasma device is an atmospheric pressure plasma device, preferably a dielectric barrier discharge device, an array, a jet, or an arc, more preferably a dielectric barrier discharge device.

Plasma devices are commercially available, for example from Cinogy, Duderstadt, Germany, from NeoplasTools, Greifswald, Germany, or from Electronic Diener, Ebhausen, Germany.

In a further preferred embodiment, the aqueous liquid is treated with the plasma device for 1 min to 24 hours, preferably 2 min to 180 min, more preferably 3 to 30 min, most preferably 5 to 15 min.

In a further preferred embodiment, the plasma device uses a frequency of 30 to 20,000 Hz, preferably 30 to 700 Hz, more preferably 150 to 700 Hz, more preferably 150, 200, 300, 400, 500, 600 or 700 Hz, most preferably 300 Hz and/or
   a voltage of 0.2 to 25 kV peak-to-peak, preferably 6 to 17 kV, more preferably 10 to 14.5 kV, more preferably 10, 11, 12, 13, 13.5, 14, or 14.5 kV, most preferably 13.5 kV and/or a power of 1 to 10,000 mW, preferably 50 to 200 mW, more preferably 100 mW.

In a further preferred embodiment, the $H_2O_2$ concentration of the obtained aqueous liquid is 0.05 to 5 mM, preferably 0.2 to 2.0 mM, more preferably 0.4 to 1.5 mM.

In a preferred embodiment according to item 1, the aqueous liquid is KPi buffer, the at least one enzyme is HRP and the at least one organic compound is guaiacol.

In a further preferred embodiment according to item 1, the aqueous liquid is KPi buffer, preferably 10 mM to 1 M KPi buffer, more preferably 100 mM KPi buffer, preferably with a pH value of 4 to 8, more preferably of 4 to 7, and most preferably of 6 or 7. In step i), the aqueous liquid comprises at least one enzyme, preferably, the enzyme is HRP, preferably HRP is available in a concentration of 0.05 to 5 U $mL^{-1}$ in the aqueous liquid, more preferably in a concentration of 0.5 to 2 U $mL^{-1}$. The aqueous liquid comprises at least one organic compound, preferably guaiacol, preferably in a final concentration of 1 to 200 mM, more preferably in a concentration of 5 to 100 mM. Preferably, samples of the aqueous liquid, comprising at least one enzyme and at least one organic compound can be treated with a plasma device, preferably with a DBD plasma device to generate $H_2O_2$, which can be directly converted by HRP to produce oxidized organic compounds (see FIG. 6).

In another preferred embodiment according to item 3, the aqueous liquid is KPi buffer, the at least one enzyme is UPO and the at least one organic compound is ethylbenzene.

In another preferred embodiment according to item 3, the aqueous liquid is KPi buffer, preferably 10 mM to 1 M KPi buffer, more preferably 250 mM KPi buffer, preferably with a pH value of 4 to 8, more preferably of 4 to 7, and most preferably of 6 or 7. In step i), the aqueous liquid is treated with the plasma device, preferably a DBD device, preferably for different amounts of time, typically 5 minutes. Then the sample was let to rest in step ii), preferably for five minutes, preferably at room temperature. In step iii), at least one organic compound, preferably ethylbenzene, preferably in a final concentration of 0.1 to 200 mM, more preferably 0.5 to 100 mM, and at least one enzyme, preferably the unspecific peroxygenase, which has preferably a final enzyme concentration of 0.1 to 500 µM, more preferred 0.1 to 200 µM, are added to the aqueous liquid comprising $H_2O_2$ from step ii). In step iv), the mixture obtained was incubated, preferably for 1 to 30 minutes, more preferably for 10 minutes, preferably at 20 to 40° C., more preferably at 30° C. and preferably at 100 to 1000 rpm, more preferably at 500 to 700 rpm. Preferably, plasma-activated buffer was added several times and the reaction was incubated preferably for 1 to 30 minutes, more preferably for 10 minutes.

In another preferred embodiment according to item 3, the aqueous liquid, comprising at least one organic compound, is KPi buffer. The organic compound is preferably ethylbenzene, preferably in a final concentration of 0.1 to 200 mM, more preferred in a final concentration of 0.5 to 100 mM. In this embodiment, in step i) the aqueous liquid, comprising at least one organic compound, is treated with the plasma device, preferably a DBD device, preferably for different amounts of time, typically 5 minutes. Then the sample is let to rest in step ii) for 1 second to 30 minutes, preferably at room temperature. In step iii), the at least one enzyme is added to the aqueous liquid comprising $H_2O_2$ and at least one organic compound, obtained in step ii). Preferably, the enzyme is immobilized, more preferred the enzyme is the immobilized unspecific peroxygenase. In step iv) of the embodiment, the mixture is incubated, preferably for 1 to 30 minutes, more preferred for 10 minutes, preferably at 20 to 40° C., more preferred at 30° C. and preferably at 100 to 1000 rpm, more preferred at 500 to 700 rpm. Preferably, plasma-activated buffer was added several times, more preferably 3 to 7 times to the reaction mixture. Further preferred, the immobilized enzyme is positioned distant to the surface of the aqueous liquid, which is in proximity to the plasma device; wherein the immobilized enzyme is located between 1 mm and 20 cm from the surface of the aqueous liquid, preferably at the bottom of a reaction chamber or vessel containing the aqueous liquid in which the aqueous liquid is treated, or a reaction channel or tube through which the aqueous liquid is flowing during treatment; wherein the enzyme is preferably immobilized on a solid support, more preferably the enzyme is covalently linked to the solid support or embedded in a polymeric structure, most preferably the enzyme is immobilized by covalent attachment to EC-HA Sepabeads using glutaraldehyde as linker.

Optionally, the mixture obtained in step ii) of item 1 or step iv) of item 3 is extracted to isolate the oxidized organic compound. Preferred extraction agents are ethyl acetate, dichloro methane, methanol, ethanol, and petrol ether. In particular, ethyl acetate is used.

Alternatively, all other separation processes that are known to the person skilled in the art to separate the oxidized or hydroxylated organic compounds from the aqueous liquid can be used.

All items and embodiments described herein in the context of the methods are also applicable to the described use of a plasma device, for producing aqueous liquid comprising $H_2O_2$ for use in an enzymatic reaction.

BRIEF DESCRIPTION OF THE DRAWINGS

The accompanying drawings serve to afford an understanding of various embodiments. The drawings illustrate embodiments and together with the description serve to elucidate same. Further embodiments and numerous advantages from among those intended are evident directly from the following detailed description. The elements and structures shown in the drawings are not necessarily illustrated in a manner true to scale with respect to one another.

DETAILED DESCRIPTION

Examples

Example 1

Production of Unspecific Peroxygenase (UPO)

Figure 1:
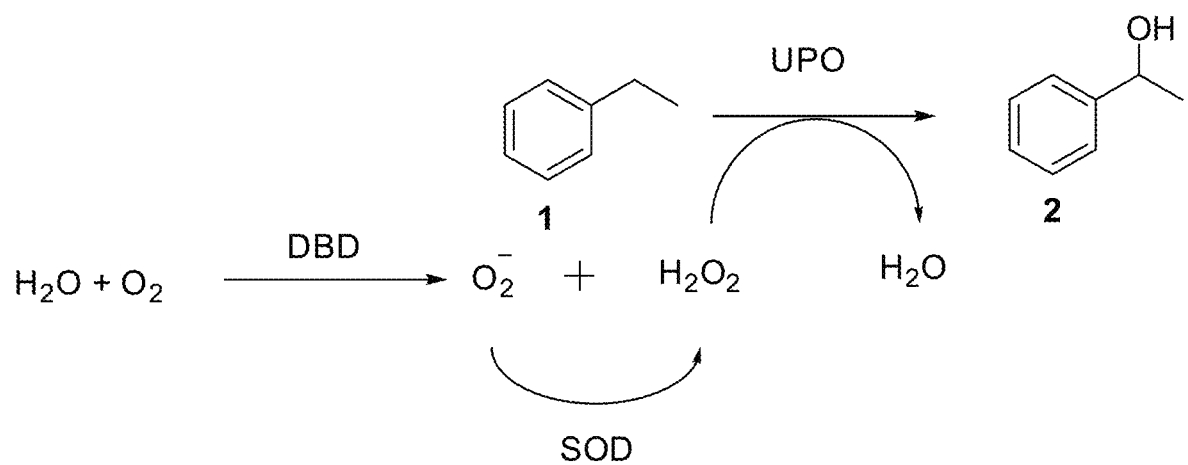
FIG. 1: General scheme of the reaction, which forms the basis of Example 1: The DBD treatment of an aqueous liquid produces $H_2O_2$ and superoxide, the latter of which can be converted into $H_2O_2$ by SOD. The peroxide is then used to fuel the UPO catalyzed hydroxylation of ethylbenzene to 1-(R)-phenylethanol.

UPO from the fungus Agrocybe aegerita was produced as reported in Molina-Espeja et al., Enzyme Microb. Technol., 2015, 73, 29-33.

The purity of the protein was tested by SDS-PAGE. Two bands were found in the gel, which correspond to the two isoforms of the protein as described in Pecyna et al., Appl. Microbiol. Biotechnol., 2009, 84, 885-897.

Plasma-Driven Reactions

In general, a solution of potassium phosphate buffer (110 µL, 250 mM, pH 7.0) was treated with the DBD (dielectric barrier discharge) device for different amounts of time (typically 5 minutes). The used DBD device has one driven, cylindrical copper electrode covered with aluminum oxide with a total diameter of 20 mm. Plasma was generated by applying voltage pulses with a maximum of ~13.5 kV, a trigger frequency of 300 Hz and a surface power density of 130 mW/cm$^2$.

Then the sample was let to rest for five minutes at room temperature in order to eliminate the short-lived species produced by the plasma. The plasma-activated buffer obtained (110 μL) was combined with ethylbenzene (5 μL for a total concentration of 80 mM) and a solution of unspecific peroxygenase (final enzyme concentration 100 μM) to a total volume of 150 μL and incubated for 10 minutes at 30° C. and 600 rpm. Plasma-activated buffer was added two times (100 μL) and the reaction was incubated for 10 minutes. The final reaction volume (355 μL) was extracted with ethyl acetate containing 1-octanol (2 mM) as injection standard and analyzed by gas chromatography. The organic phase was dried with $MgSO_4$ and measured with a Shimadzu 2010 GC system containing a Hydrodex-β-6TBDM column (Macherey-Nagel, Germany) with a column temperature of 120° C.

Effect of the Plasma Treatment Time in the Production of 1-(R)-Phenylethanol

TABLE 1

Effect of the plasma treatment time in the production of 1-(R)-phenylethanol using a solution of purified UPO (100 μM) in different conditions. Plasma treatment performed at room temperature. Hydroxylation reaction performed at 30° C. and 600 rpm.

| Entry | Treatment time (min) | Buffer (mM) | pH | Final 1-phenylethanol concentration (mM) | TTN |
|---|---|---|---|---|---|
| 1 | 0 | KPi 250 mM | 7 | 0 | 0 |
| 2 | 5 | KPi 250 mM | 7 | 0.46 ± 0.01 | 4576 |
| 3 | 10 | KPi 250 mM | 7 | 0.97 ± 0.00 | 9729 |
| 4 | 15 | KPi 250 mM | 7 | 1.28 ± 0.05 | 12868 |
| 8 | 5 | KPi 1M | 7 | 0.53 ± 0.04 | 5336 |
| 9 | 5 | KPi 250 mM | 7 | 0.62 ± 0.02 | 6245 |
| 10 | 5 | KPi 50 mM | 7 | 0.55 ± 0.00 | 5475 |
| 11 | 5 | TRIS 50 mM | 7 | 0.69 ± 0.01 | 6864 |
| 12 | 5 | HEPES 50 mM | 7 | 0.89 ± 0.06 | 8913 |
| 13 | 5 | MES 50 mM | 7 | 0.64 ± 0.01 | 6368 |

The product formation correlates with the plasma treatment time, showing the accumulation of 1-(R)-phenylethanol (Table 1, Entry 1 to 4). In all cases the product is optically pure (ee>99%), which suggests that the hydroxylation reaction is based on an enzymatic reaction. Calculated total turnover numbers confirm that this is comparable to previously reported TTNs of UPO. Negative controls without enzyme, plasma treatment or ethylbenzene did not result in any detectable product formation.

In the experiments, buffered solutions were used. Variations of the pH from pH 4 to 8 and the buffer salt concentration of the potassium phosphate buffer had an influence on product formation. Different buffer salts and concentrations were tested (potassium phosphate, TRIS, HEPES, MES, Table 1, Entries 8-11). While TRIS-buffer and MES-buffer show a small improvement over potassium phosphate buffer, the use of HEPES proved to be the best performing buffer for the reaction yielding 62% more product than using KPi.

Peroxide-Formation with the Aid of Additional Enzymes

Reactive oxygen species can interact directly with the peroxygenase resulting in amino acid modifications or complete inactivation of the enzyme. This drawback can be overcome by different approaches, like the addition of other detoxifying enzymes, shielding the peroxygenases against the short-living reactive species, or adjustments in the plasma generation. For example, the superoxide dismutase A (SOD) from *Escherichia coli* can further increase the peroxide production by conversion of plasma-generated superoxide to $H_2O_2$.

The addition of different amounts of SOD during the plasma treatment resulted in a slight increase of the formation of 1-phenylethanol.

TABLE 2

Effect of the addition of superoxide dismutase (SOD) in the production of 1-phenylethanol.

| Entry | SOD concentration (mg/mL) | SOD addition | Formation of 2-phenylethanol (mM) |
|---|---|---|---|
| 1 | 0 | — | 0.4 |
| 2 | 0.5 | After treatment | 0.4 |
| 3 | 0.5 | During treatment | 0.47 |
| 4 | 1 | During treatment | 0.5 |

Comparison of External Addition of Plasma-Activated Buffer and In Situ $H_2O_2$ Generation Two different methods of $H_2O_2$ provision to the biocatalyst were performed in comparison:
1. The buffer was treated with plasma and then added to a vial containing the UPO and ethylbenzene.
2. A solution containing the enzyme and ethylbenzene was directly placed under the DBD and treated for an equivalent amount of time with plasma.

With both methods, product was obtained. However, in the first method, 9 times more product was produced.

Plasma-Driven Biocatalysis with Immobilized UPO

To provide an improved product formation of method 2, immobilized UPO was used. The UPO immobilization was carried out in EC-HA Sepabeads generously provided by Viazym (Delft, Netherlands) using the protocol provided by the manufacturer. 10 mg of carrier were used to immobilize 0.35 mM of enzyme. This amount of carrier was then used in 500 μL of reaction volume to a final enzyme concentration of 0.7 μM. After the addition of 5 μL of ethylbenzene (80 mM), 100 μL of the reaction volume were extracted (without removing the immobilized protein) and treated for 5 minutes with the DBD. After treatment, the sample was placed back in the reaction vial and incubated for 10 minutes at 30° C. and 600 rpm. Then the treatment was repeated between 3 and 7 times. Due to the immobilization, this step could be performed while keeping the enzyme in the reaction vial. As positive control, the reaction was carried out using free enzyme in the same concentrations and with 3 cycles of treatment as described previously.

Figure 2:
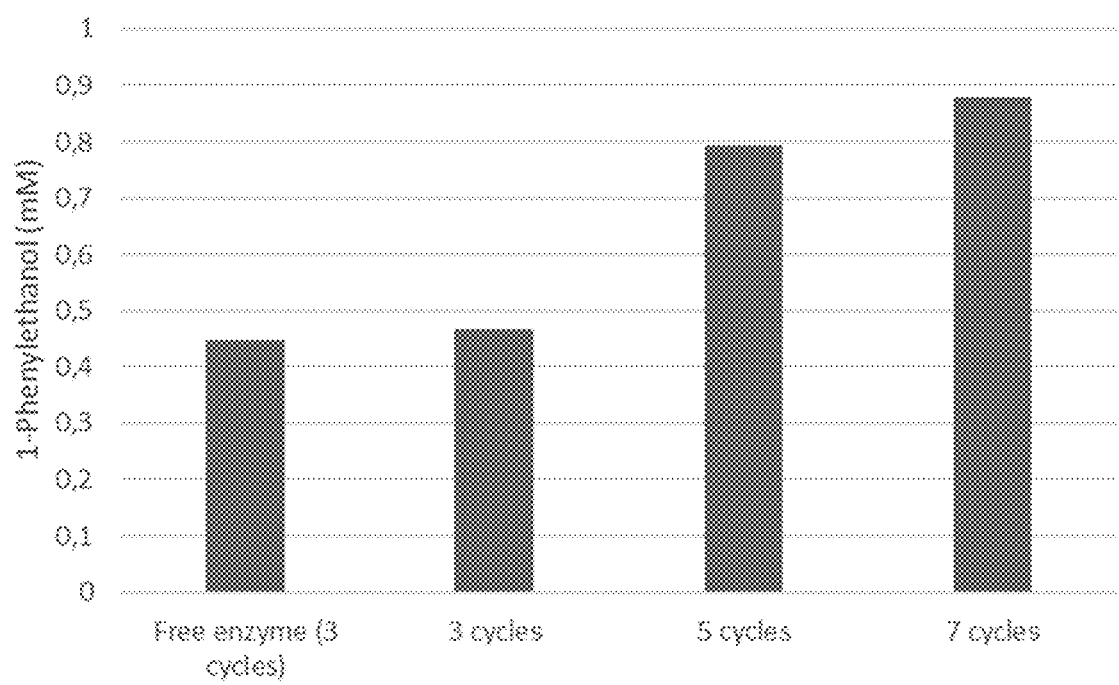
FIG. 2: Concentration of 1-phenylethanol after different cycles of DBD plasma treatment either with free or immobilized enzyme of UPO.
Figure 3:
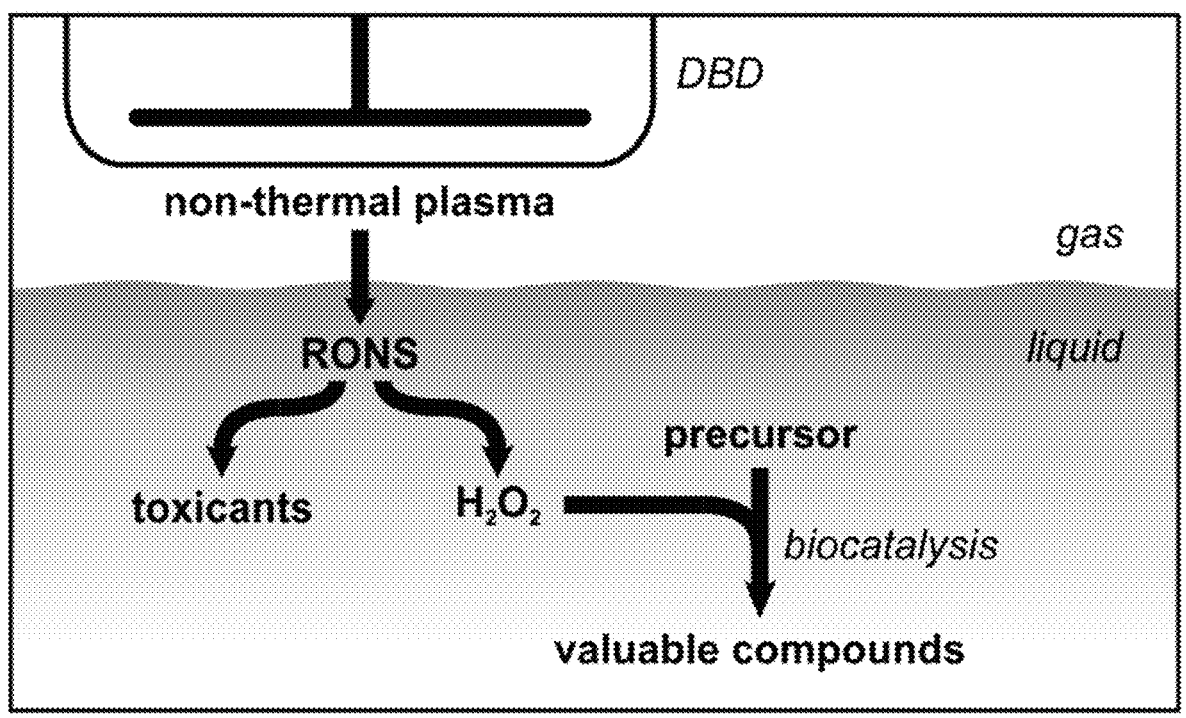
FIG. 3: General scheme of the plasma-driven $H_2O_2$ generation and the subsequent biocatalysis, which forms the basis of Example 2. A dielectric barrier discharge (DBD) is generating non-thermal plasma, interacting with the liquid and thus forming reactive oxygen and nitrogen species, e.g. peroxynitrite ($ONOO^-$), superoxide ($O^{2-}$), or $H_2O_2$. Some of the species can recombine or dissociate to the other reactive particles. Some ROS or RNS can serve as reactants fueling ROS- or RNS-dependent biocatalyses.

This strategy obtained the same amount of product than with external addition of plasma-activated buffer without diluting the reaction solution (method 1), which is a decisive advantage for any synthetic application. The product obtained in both cases presented an ee of >99%, indicating that the plasma treatment does not interact or racemize the 1-(R)-phenylethanol. Up to seven treatment cycles were tested, producing an accumulation of 1-phenylethanol up to a concentration of 0.88 mM (FIG. 2).

Example 2

Horseradish peroxidase extracted from horseradish roots was obtained from Sigma-Aldrich (P8375) as lyophilized powder.

Dielectric Barrier Discharge (DBD)

The used DBD device has one driven, cylindrical copper electrode covered with aluminum oxide with a total diameter of 20 mm. Plasma was generated by applying voltage pulses with a maximum of ~13.5 kV, a trigger frequency of 300 Hz and a surface power density of 130 mW/cm$^2$.

H$_2$O$_2$-Accumulation in DBD-Treated Water and KPi Buffer

Figure 4:
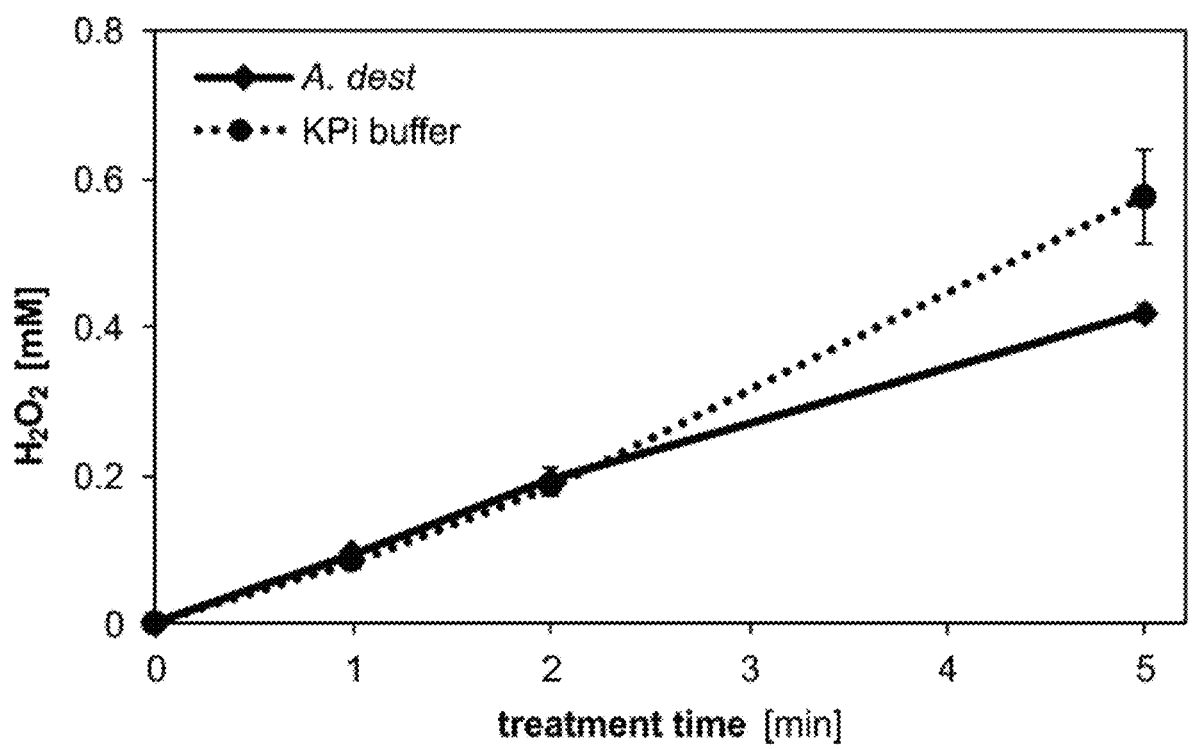
FIG. 4: $H_2O_2$ accumulation in DBD-treated water and KPi buffer (100 mM, pH 6).

H$_2$O$_2$-accumulation was determined in DBD-treated water and KPi buffer (100 mM, pH 6). Samples of 200 µL were placed onto a glass slide and treated with DBD plasma for the indicated amount of time (FIG. 4). Immediately after treatment, the samples were analyzed with a commercially available hydrogen peroxide test kit, following the manufacturer's instructions (Merck Spectroquant Hydrogen Peroxide). The H$_2$O$_2$-concentration was determined using a calibration curve.

The overall production rate was about 0.1 mM min$^{-1}$ for both deionized water and KPi buffer. After 5 minutes, more H$_2$O$_2$ was accumulated in KPi buffer (FIG. 4). This result is explainable by the pH stabilizing effect of KPi buffer in contrast to deionized water.

Conversion of Colorimetric HRP Substrates by DBD Plasma Treatment

Figure 5:
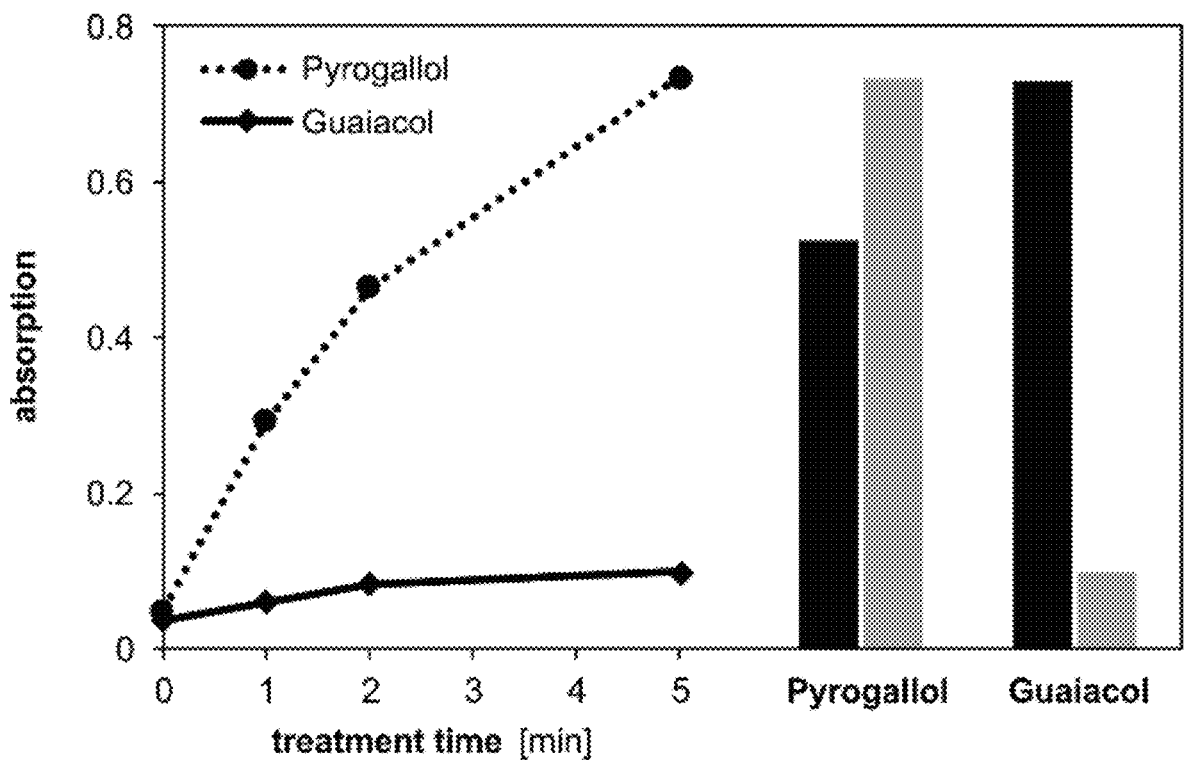
FIG. 5: Conversion of colorimetric HRP substrates by DBD plasma treatment in the presence and absence of HRP. Bars in the right panel show the absorption after 5 minutes of plasma treatment in the presence (black) and absence (grey) of HRP.

In the experiment, colorimetric HRP substrates were converted by DBD plasma treatment in the presence and absence of horseradish peroxidase (HRP). Pyrogallol (PG) and guaiacol (GC) were prepared in KPi buffer at 100 mM and 10 mM, respectively. For each substrate 100 µL were treated with the DBD device for the indicated amounts of time (FIG. 5). Directly after treatment, the samples were analyzed photometrically using the respective absorption maxima ($\lambda_{Pyrogallol}$=420 nm, $\lambda_{Guaiacol}$=470 nm). The enzymatic conversion was determined by adding 50 µL of substrate (20 mM and 200 mM for GC and PG, respectively) into a microtiter plate well, mixing with 50 µL of 2 mM H$_2$O$_2$, subsequent addition of 1 µL of 10 U mL$^{-1}$ HRP solution and immediate determination of the absorption.

Pyrogallol (PG) was found to be converted to the violet product purpurogallin to a significant extend by plasma treatment alone, even without HRP being present. After 5 minutes of plasma treatment of PG, the absorption was higher than for the enzymatic conversion with HRP and liquid H$_2$O$_2$. Guaiacol (GC) proved to be sufficiently plasma-stable. GC was transformed by HRP plasma-dependently (FIG. 5).

HRP Activity Under Direct Plasma Treatment

Figure 6:
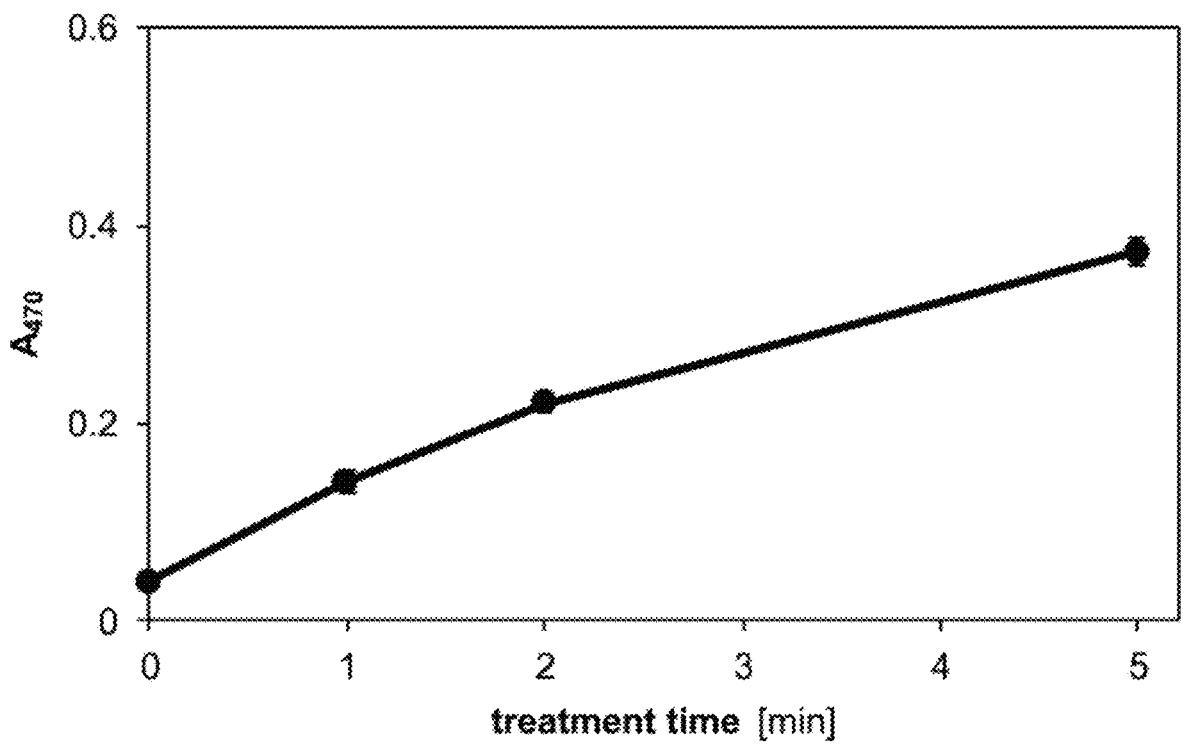
FIG. 6: Plasma-driven biocatalysis using HRP as biocatalyst (1 U mL$^{-1}$) and guaiacol (10 mM) as substrate, which are directly exposed to plasma in the KPi buffer system (100 mM, pH 6). Reaction volumes of 200 µL were treated with DBD plasma for the indicated times. Immediately after plasma treatment, the absorbance at 470 nm was measured.

In this experiment, HRP and the substrate guaiacol were directly exposed to plasma. HRP was diluted to 1 U mL$^{-1}$ in KPi buffer (100 mM, pH 6) and GC was added to a final concentration of 10 mM. Reaction volumes of 100 µL were treated with DBD plasma for the indicated times (FIG. 6). Immediately after plasma treatment, the absorbance at 470 nm was measured.

With increased plasma treatment time, absorption at 470 nm increases, indicating conversion of GC to tetraguaiacol (tGC). HRP thus is able to utilize plasma-generated H$_2$O$_2$ in the reaction. Additionally, the enzyme was not inactivated within 5 min of DBD plasma exposure (FIG. 6).

Example 3

Figure 7:
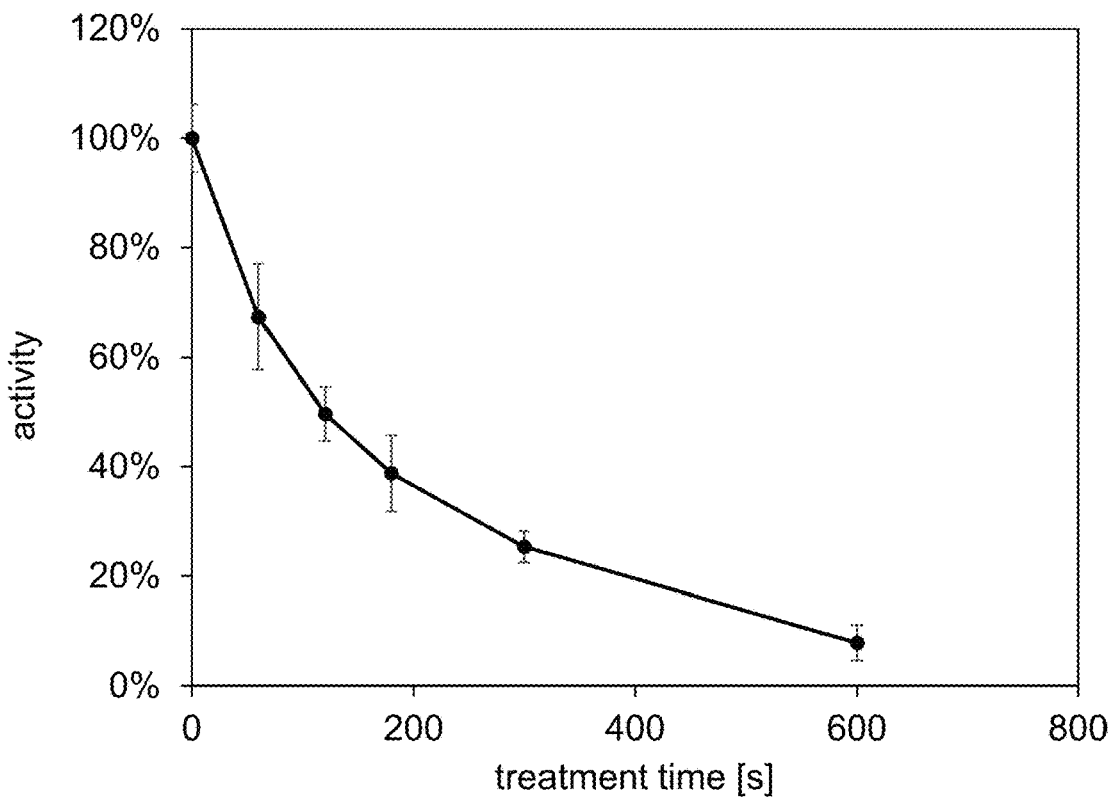
FIG. 7: Plasma treatment of unknown peroxidase (40 µL of 1 mg/mL protein solution, 2 mm distance, 13.5 kV, 300 Hz, enzyme activity against treatment time [s]).
Figure 8:
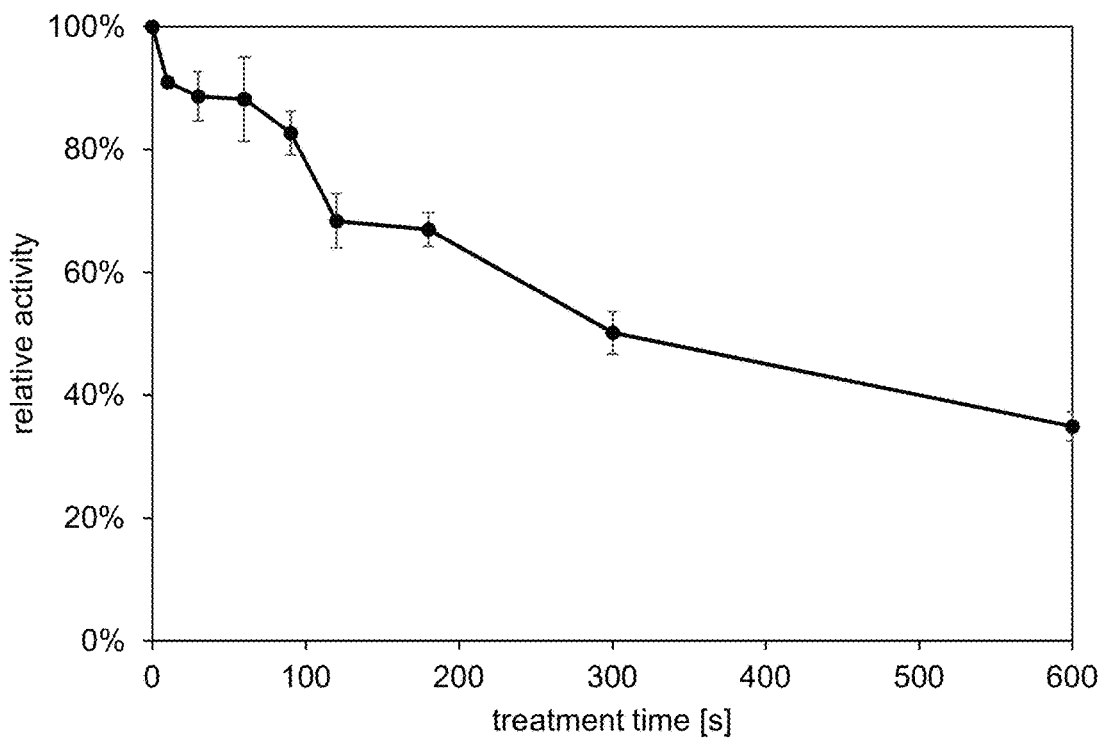
FIG. 8: Plasma treatment of unspecific peroxygenase from Agrocybe aegerita (UPO) (40 µL of 1 mg/mL protein solution, 2 mm distance, 13.5 kV, 300 Hz, relative activity against treatment time [s]).
Figure 9A:
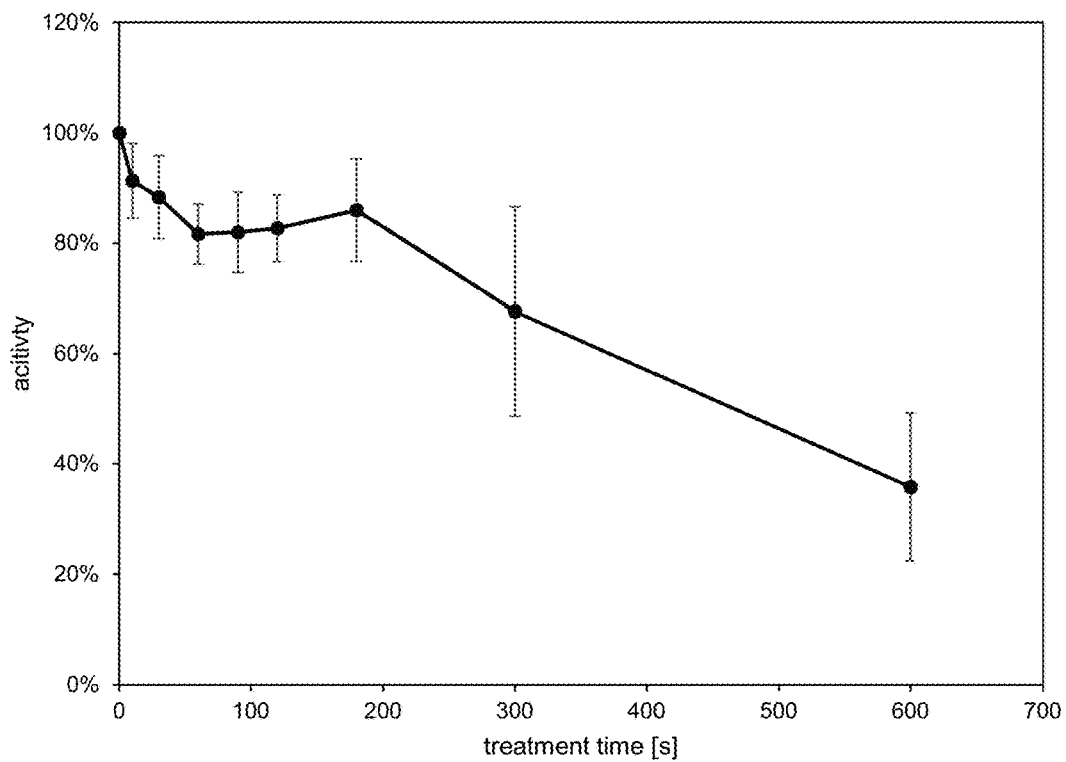
FIG. 9: Plasma treatment of vanadium chloroperoxidase from *Curvularia inaequalis* (40 µL of 1 mg/mL protein solution, 2 mm distance, 13.5 kV, 300 Hz, (9A) enzyme activity against treatment time [s], (9B) concentration against treatment time [s], (9C) fluorescence against treatment time [s]).
Figure 9B:
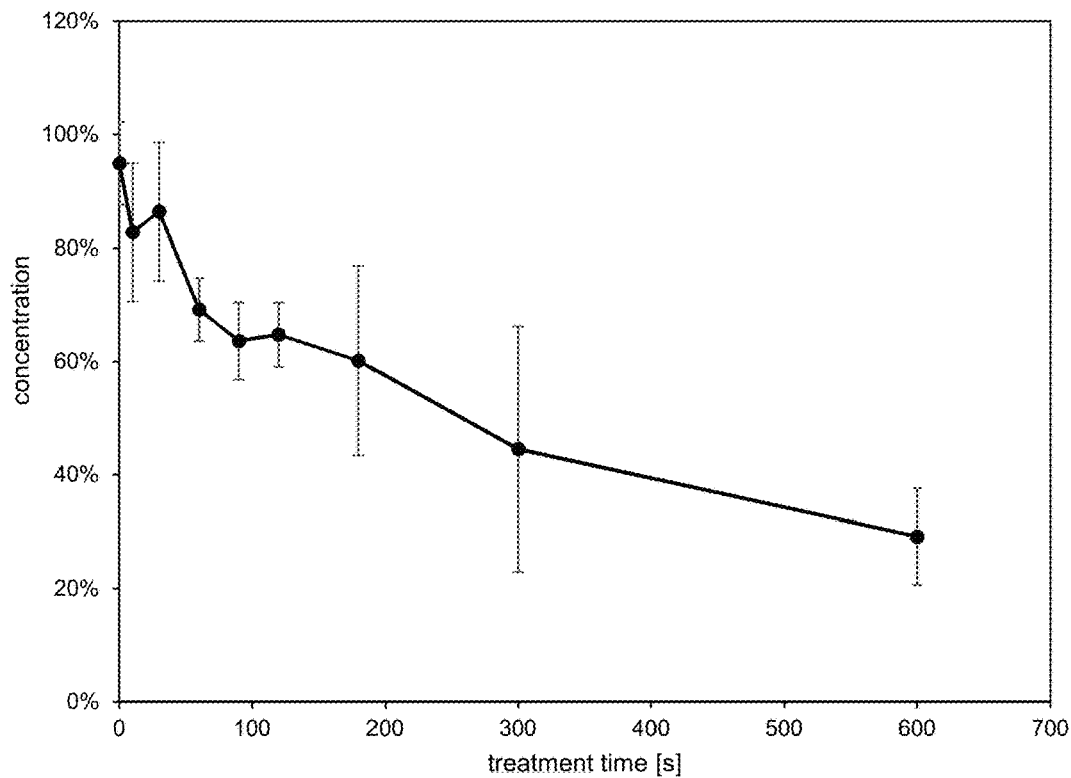
Figure 9C:
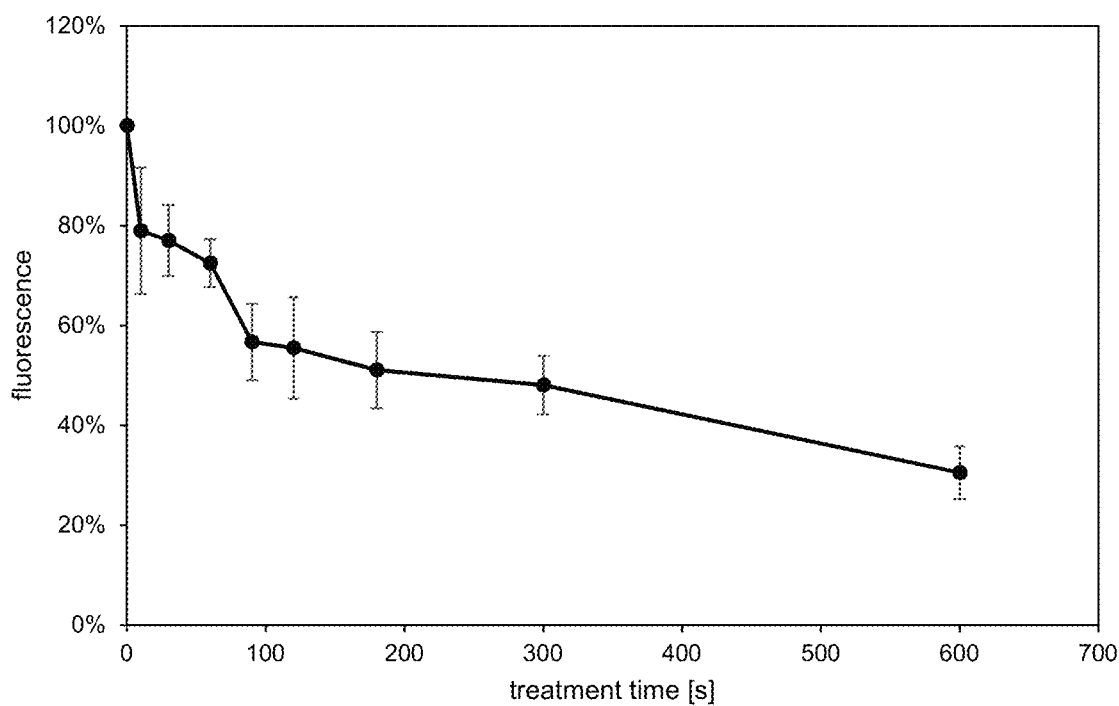
Figure 10A:
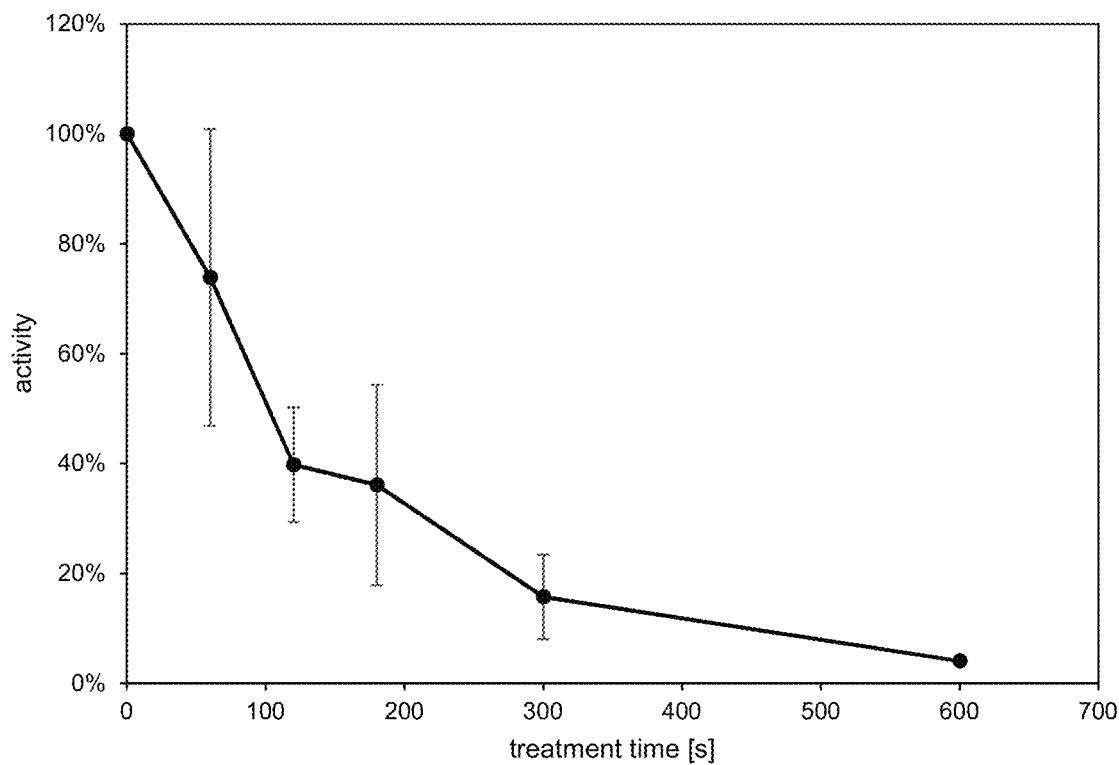
FIG. 10: Plasma treatment of ScDYP1 (40 µL of 1 mg/mL protein solution, 2 mm distance, 13.5 kV, 300 Hz, (10A) enzyme activity against treatment time [s], (10B) concentration against treatment time [s]).
Figure 10B:
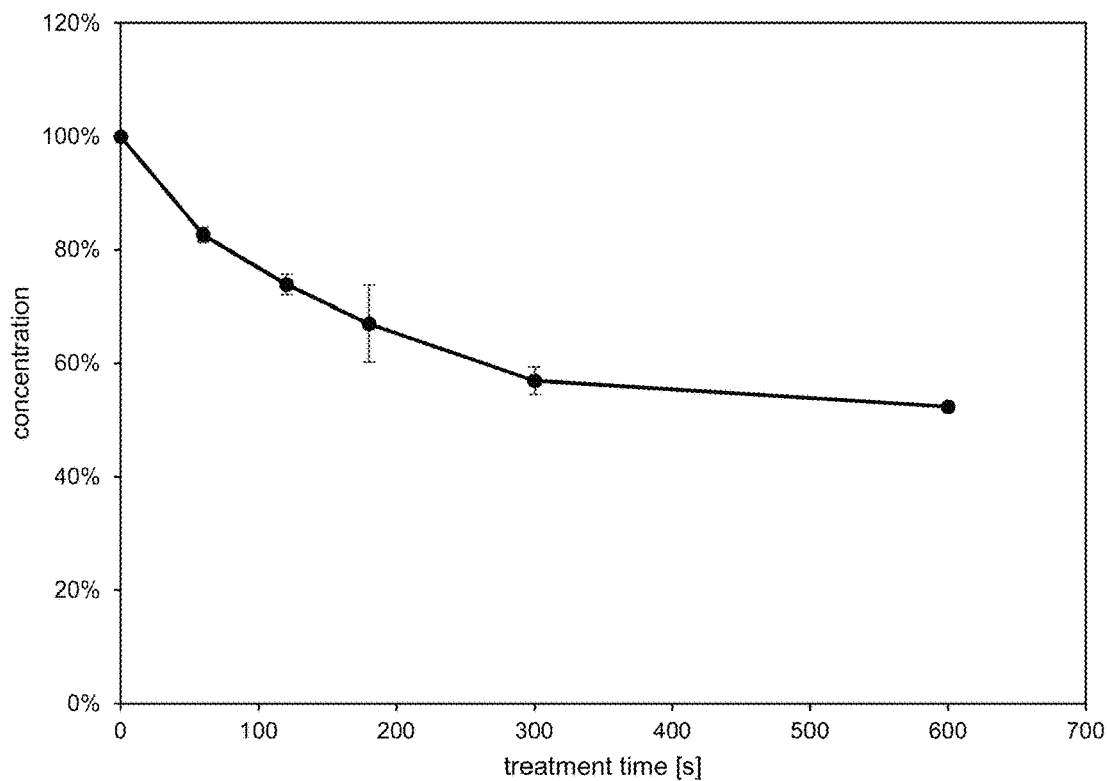
Figure 11A:
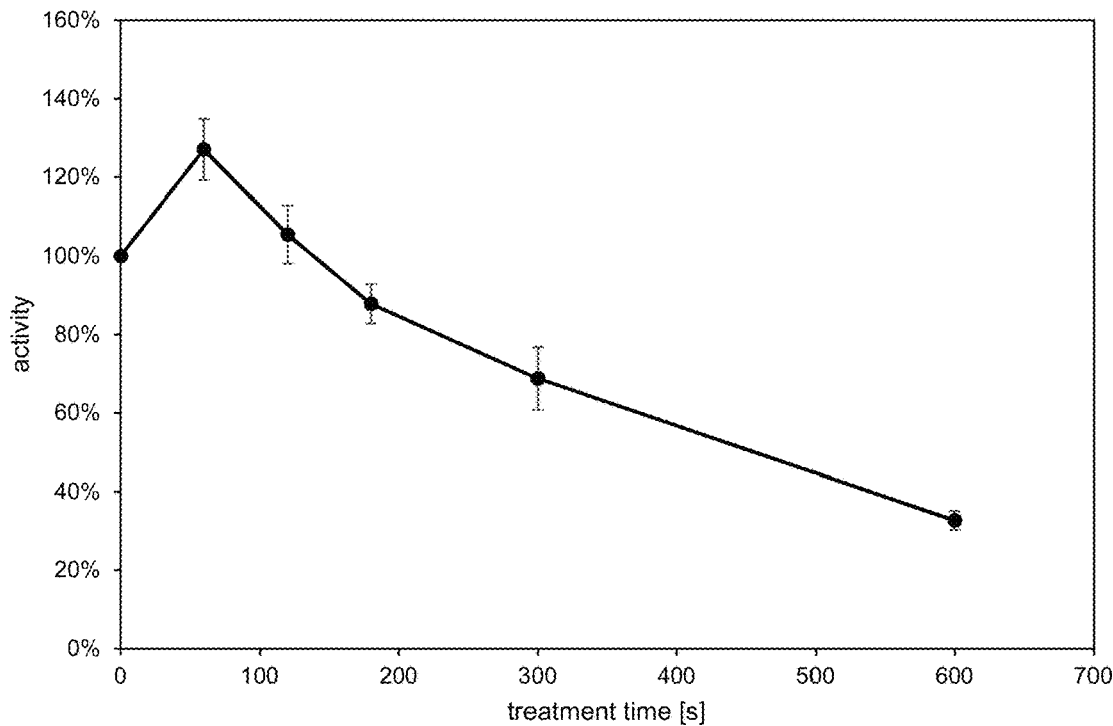
FIG. 11: Plasma treatment of ScDYP2 (40 µL of 1 mg/mL protein solution, 2 mm distance, 13.5 kV, 300 Hz, (11A) enzyme activity against treatment time [s], (11B) concentration against treatment time [s]).
Figure 11B:
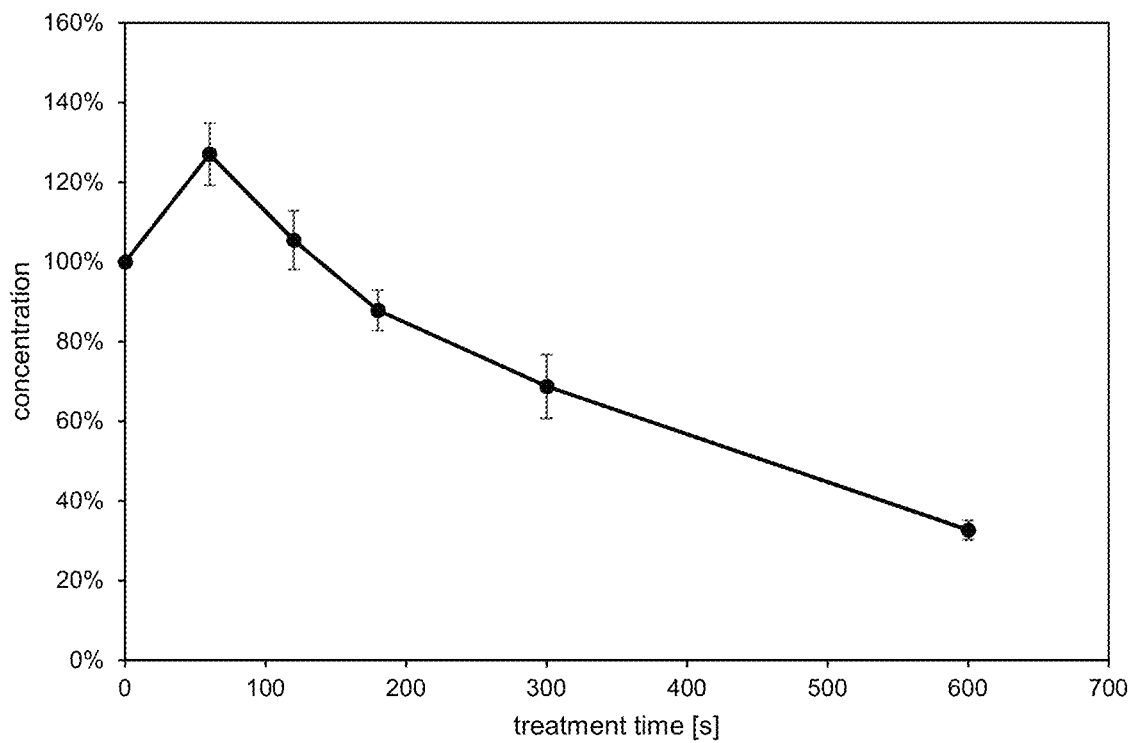

In the following, enzymes were characterized in more detail with respect to direct plasma treatment time [s]:

Unknown peroxidase (FIG. 7), unspecific peroxygenase from Agrocybe aegerita (UPO) (FIG. 8), vanadium chloroperoxidase from *Curvularia inaequalis* (FIG. 9A, 9B, 9C), DyP-type peroxidase from *Streptomyces chartreusis*, variant 1 (ScDYP1) (FIGS. 10A and 10B) and DyP-type peroxidase from *Streptomyces chartreusis*, variant 2 (ScDYP2) (FIGS. 11A and 11B) were treated with plasma with a distance between the surface of the aqueous liquid and the electrode of the plasma device of 2 mm with a voltage of 13.5 kV and a frequency of 300 Hz over 600 seconds. A total concentration of 40 µL of protein solution (1 mg/mL) was used in each case. 100% is based on the untreated enzyme.

Activity Assay Parameters:

Unknown peroxidase: 5 µL of treated sample in 2.5 mM ABTS in 50 mM sodium acetate buffer, pH 5.5; 1 mM H$_2$O$_2$; absorption measurement at 405 nm. Activity was calculated from linear slope in the absorption measurement.

UPO: 5 nM UPO; 2.5 mM ABTS in 50 mM sodium acetate buffer, pH 5.5; 1 mM H$_2$O$_2$. Activity was calculated from linear slope in the absorption measurement.

Vanadium chloroperoxidase: 10 µL of treated sample in 200 µM phenol red in 50 mM Tris-SO$_4$; 5 mM KBr and 5 mM H$_2$O$_2$. Absorption measurement at 582 nm. Activity was calculated from linear slope in the absorption measurement.

ScDYP1: 10 µL of a 1:20 dilution of the treated sample was used for activity measurements. Final concentrations: 2.5 mM ABTS in 50 mM Britton-Robinson buffer, pH 4; 200 µM H$_2$O$_2$.

ScDYP2: 10 µL of treated sample; 2.5 mM ABTS in 50 mM Britton-Robinson buffer, pH 8; 25 mM H$_2$O$_2$.

Protein concentration was determined using the Bradford method with a commercially available test kit (Roti Nano-Quant), following the manufacturer's instructions.

Fluorescence was measured with a 1:5 dilution of the treated protein, with excitation wavelength 280 nm and emission wavelength 350 nm.

In samples which were directly plasma-treated, the substrate conversion was determined by adding commercially available H$_2$O$_2$ to the sample after direct plasma treatment. The substrate used for the respective assay was added after direct plasma treatment.

Example 4

Figure 12A:
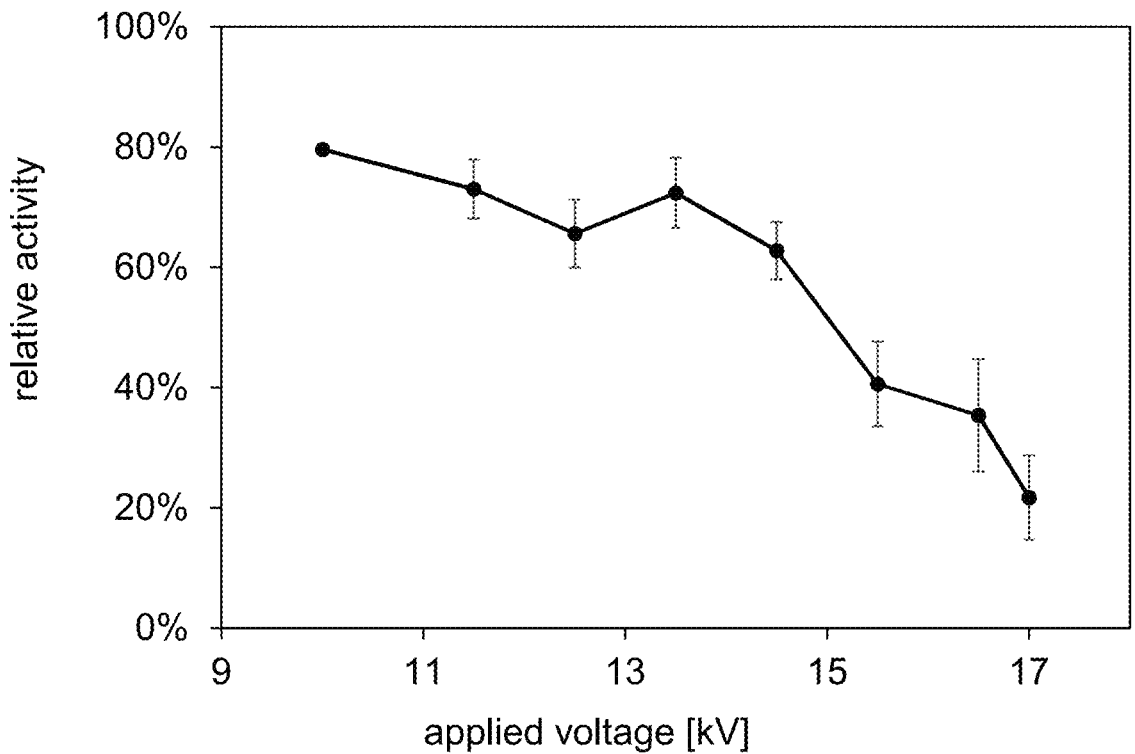
FIG. 12: Plasma tuning of horseradish peroxidase (40 µL of 10 U/mL protein solution, 2 mm distance, (12A) relative activity of HRP after 1 min of treatment at different applied voltages (kV), (12B) relative activity of HRP after 1 min of treatment at different frequencies (Hz)).
Figure 12B:
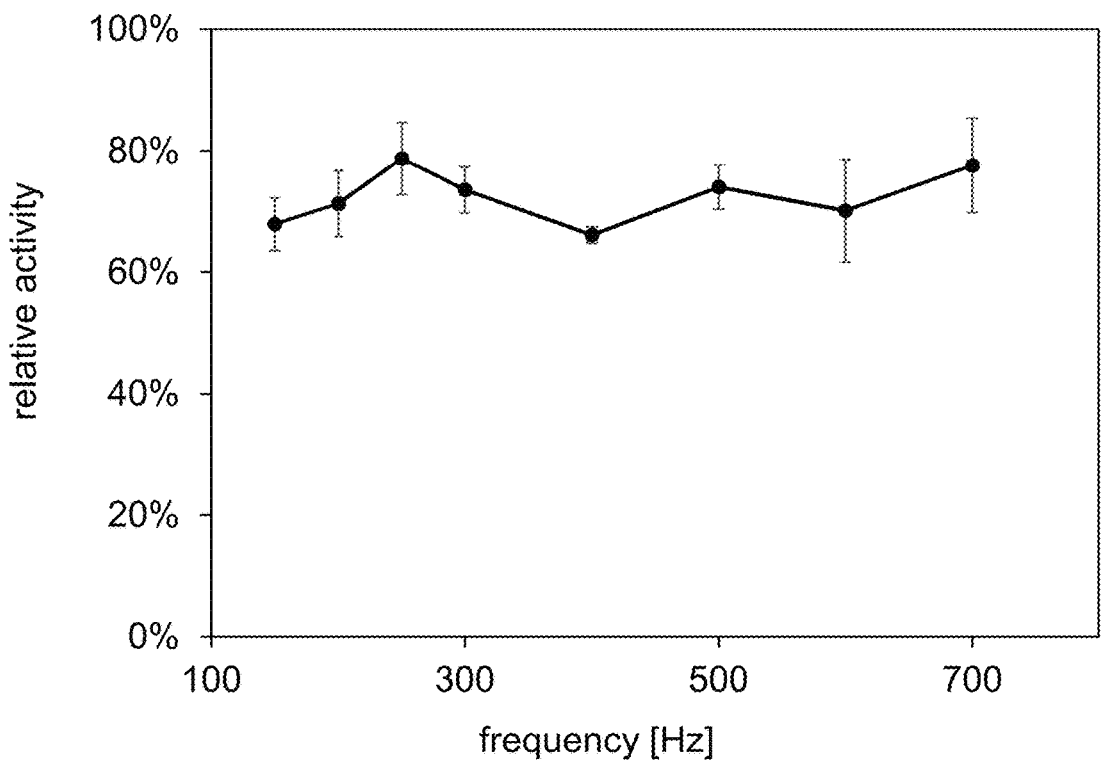

Relative activity of horseradish peroxidase (HRP) was determined after 1 min of direct plasma treatment at different applied voltages and trigger frequencies. The plasma treatment was carried out with a distance of 2 mm with 40 µL of a protein solution (10 U/mL) (FIGS. 12A and 12B).

Activity assay parameters: 2 µL of treated sample; 5 mM guaiacol (GC) in 100 mM potassium phosphate (KPi) buffer, pH 7; 0.5 mM H$_2$O$_2$.

Figure 13:
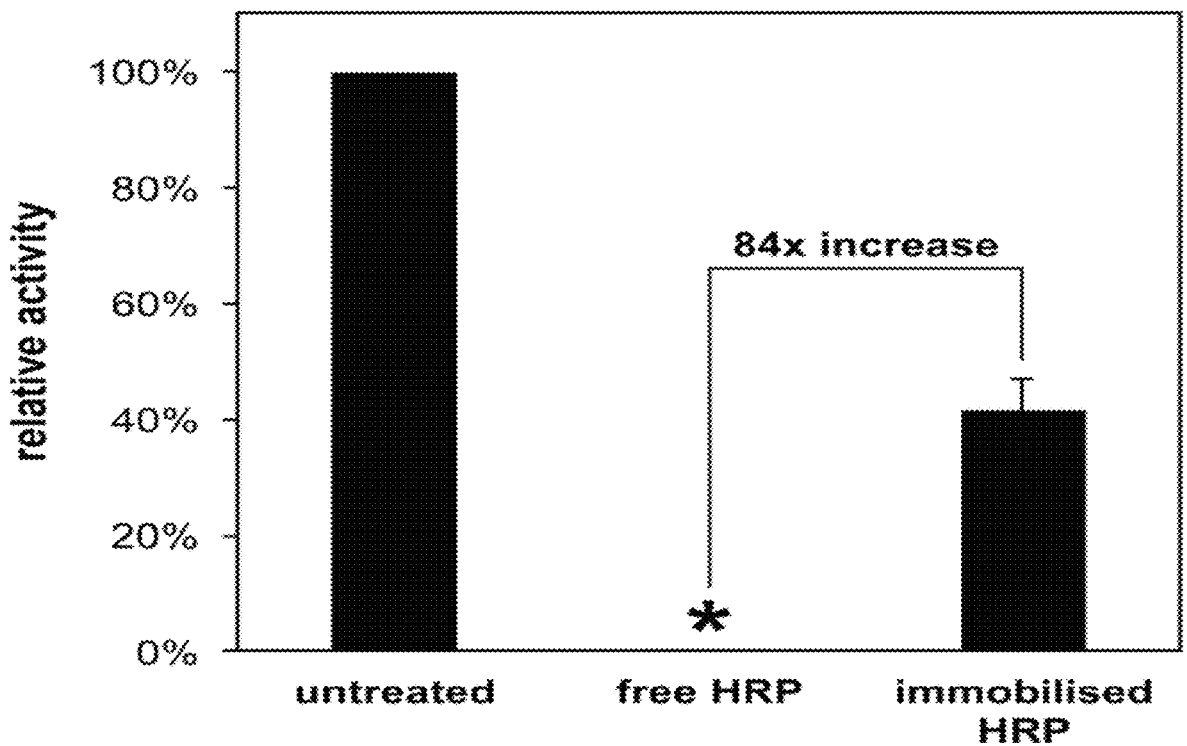
FIG. 13: Relative activity of horseradish peroxidase after treatment of free and immobilized HRP with 5 min treatment time (40 µL of 10 U/mL protein solution, 2 mm distance, 13.5 kV, 300 Hz).

Additionally, the relative activity of free and immobilized HRP after direct plasma treatment with a treatment time of 5 min (2 mm distance, 13.5 kV, 300 Hz) was determined in comparison to untreated HRP using the activity assay parameters as described above (FIG. 13).

HRP was immobilized with Relizyme HA403 M beads (Resindion, Binasco, Italy). 10 mg of beads were activated by incubating in 100 mM KPi buffer (pH 7) with 0.4% glutaraldehyde for 1 h. After washing twice with deionized water, up to 5 mg of enzyme were added in 1 mL buffer. Immobilization was carried out over night at room temperature with constant shaking. Binding efficiency was checked by measuring the protein concentration of the supernatant after incubation and was found to be >80% in all cases.

Figure 14:
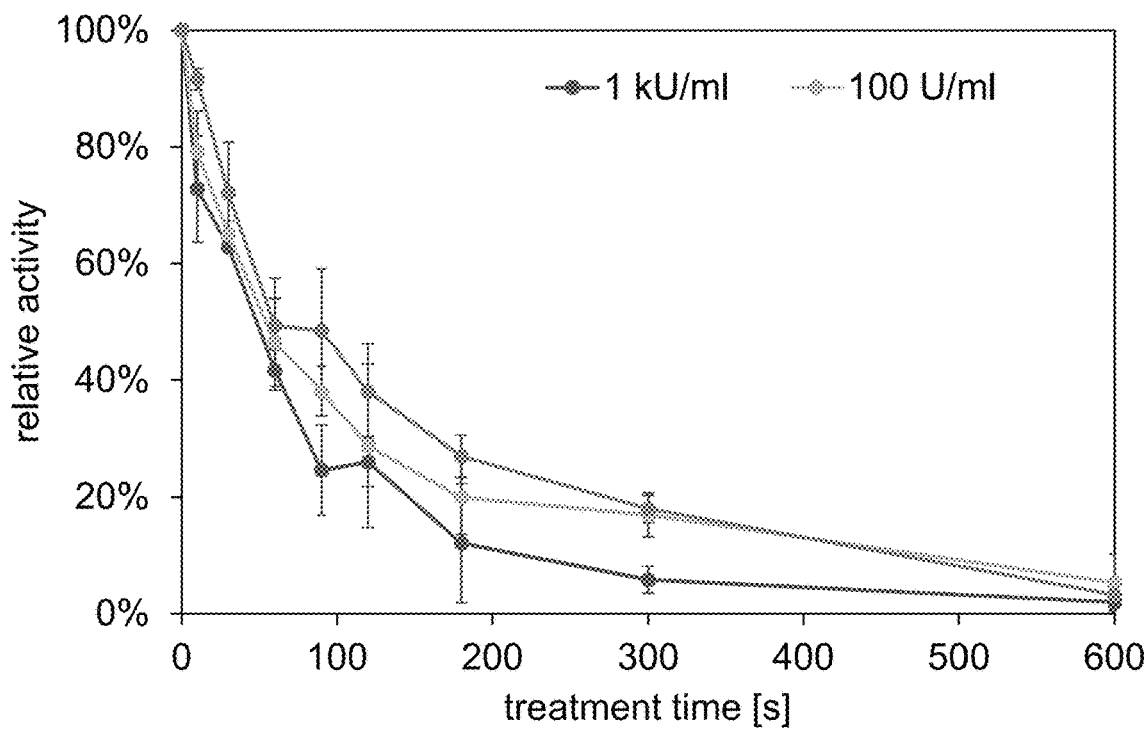
FIG. 14: Relative activity of differently concentrated HRP against treatment time [s] (40 µL of protein solution, 2 mm distance, 13.5 kV, 300 Hz).

In addition, the effect of the protein concentration (1 kU/mL, 100 U/mL, 10 U/mL) on the relative activity of HRP over the treatment time [s] was measured (40 µL of protein solution, 2 mm distance, 13.5 kV and 300 Hz using the activity assay parameters as described above (FIG. 14)).

In samples which were directly plasma-treated, the substrate conversion was determined by adding commercially available H$_2$O$_2$ to the sample after direct plasma treatment. The substrate used for the respective assay was added after direct plasma treatment.

Example 5

In the following, the products formed by plasma-driven biocatalysis using UPO were analysed (assay conditions: 150 nM UPO, 1 mM H$_2$O$_2$, 100 mM KPi, pH 7.5, 5 µL ETBE (150 µL final volume), reaction time 30 min, extraction with 150 µL ethyl acetate containing 2 mM 1-octanol as internal standard, analysis with Hydrodex β-6TBDM column).

Figure 15A:
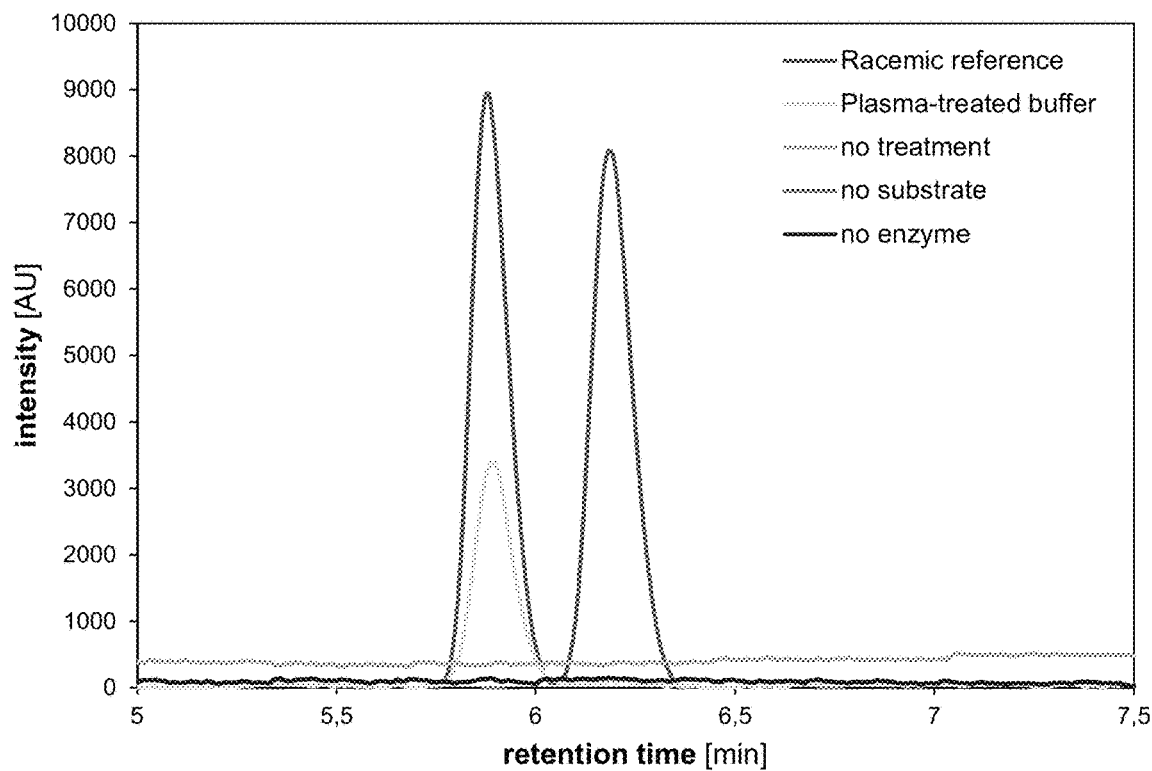
FIG. 15: Plasma-driven biocatalysis using UPO: (15A) Product analysis, (15B) Relative conversion with $H_2O_2$ or plasma-treated buffer, (15C) Reusability of the immobilized enzyme with $H_2O_2$ or plasma-treated buffer, (15D) product formation using direct plasma treatment or treatment with plasma-treated buffer (conditions: 150 nM UPO, 1 mM $H_2O_2$, 100 mM KPi, pH 7.5, 5 µL ETBE (150 µL final volume), reaction time 30 min, extraction with 150 µL ethyl acetate containing 2 mM 1-octanol as internal standard, analysis with Hydrodex β-6TBDM column).

A chromatogram illustrating the racemic product reference (1-phenylethanol), the product formation of (R)-1-phenylethanol using plasma-treated buffer, and samples without plasma treatment, without substrate and without enzyme measured by gas chromatography is shown in FIG. 15A.

Figure 15B:
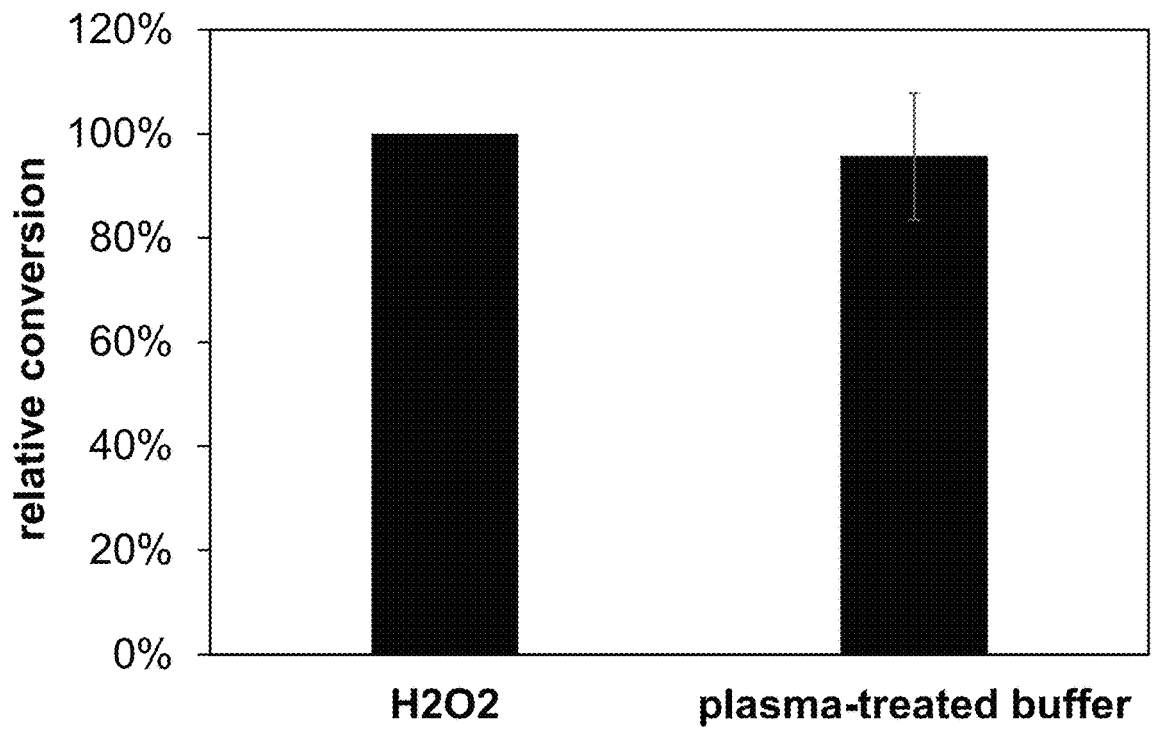

A comparison of relative conversion of UPO when using commercially available H$_2$O$_2$ or plasma-treated buffer is shown in FIG. 15B.

Figure 15C:
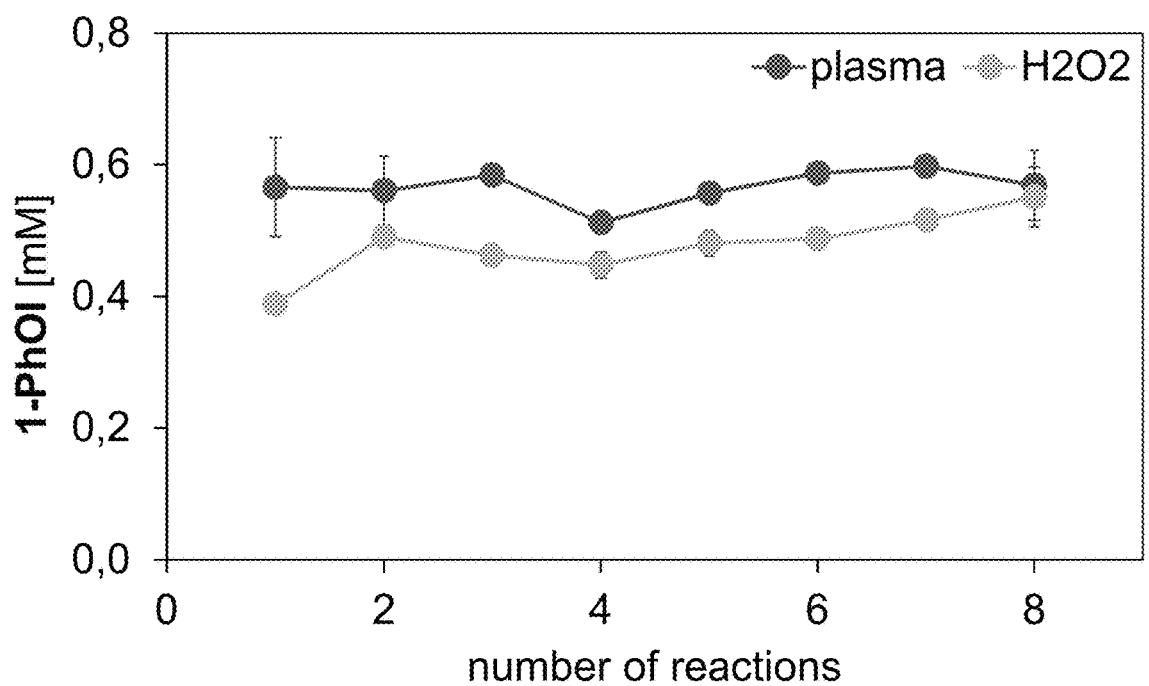

Additionally, it was determined how many cycles can be performed with the same enzyme, wherein one sample comprised plasma-treated buffer and immobilized UPO and the second sample comprised commercially available H$_2$O$_2$ and immobilized UPO. The data are illustrated in FIG. 15C.

Figure 15D:
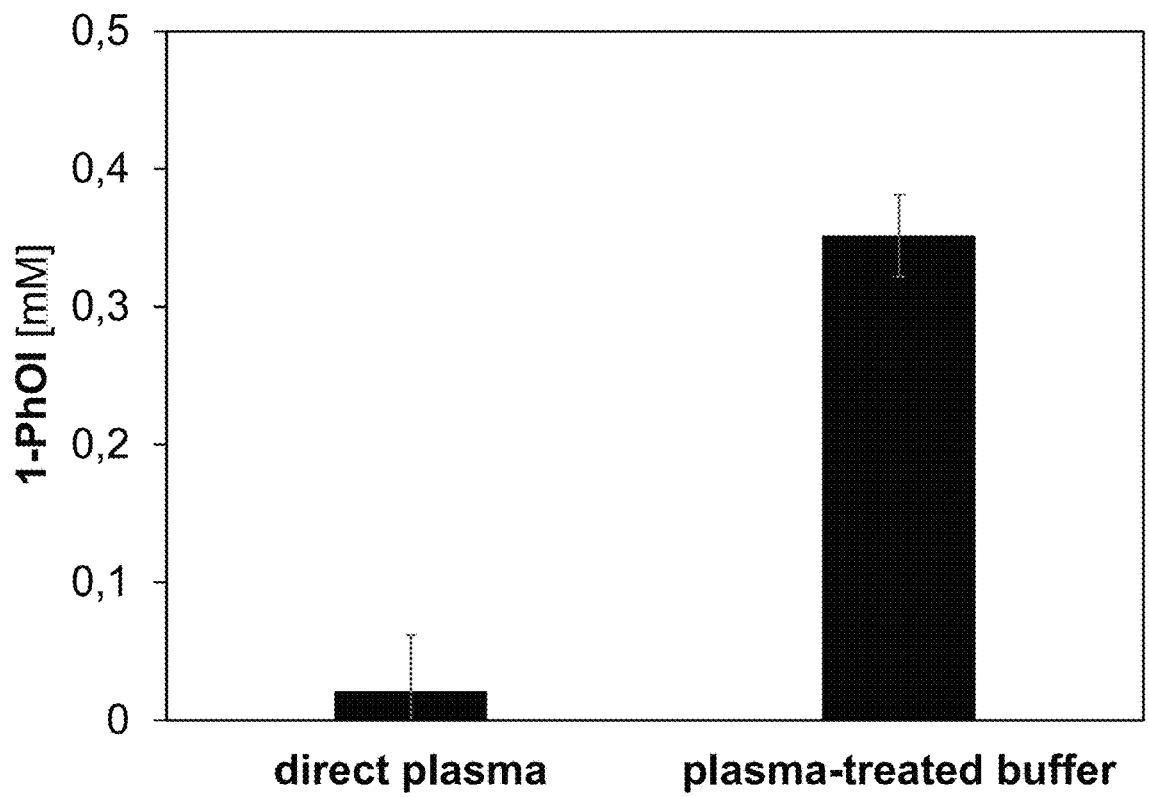

Then it was determined, whether plasma treatment can be coupled with running the reaction. For this, the 1-phenylethanol concentration formed based on direct plasma treatment was compared to the 1-PhOl concentration formed based on plasma-treated buffer (FIG. 15D). Assay conditions (15A-15D): 150 nM UPO, 1 mM H$_2$O$_2$, 100 mM KPi, pH 7.5, 5 µL ETBE (150 µL final volume), reaction time 30 min, extraction with 150 µL ethyl acetate containing 2 mM 1-octanol as internal standard, analysis with Hydrodex β-6TBDM column (GC).

In samples which were directly plasma-treated, the substrate conversion was determined by adding commercially available H$_2$O$_2$ to the sample after direct plasma treatment. The substrate used for the respective assay was added after direct plasma treatment.

Example 6

Figure 16:
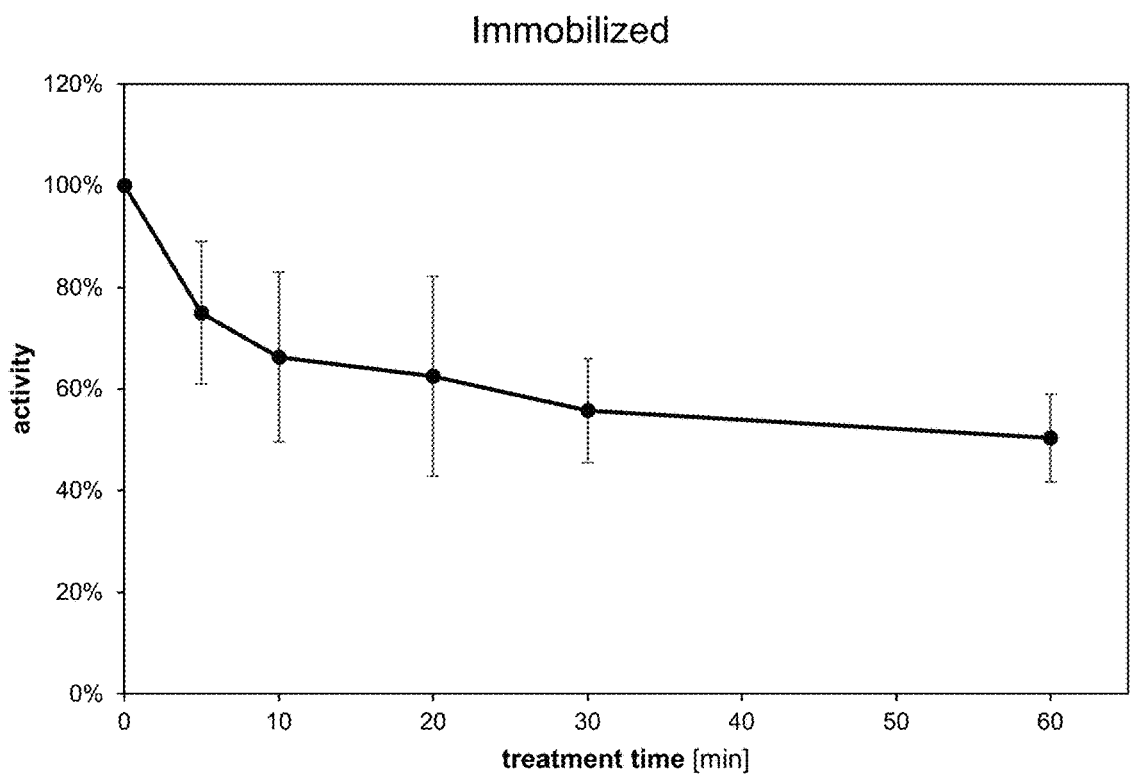
FIG. 16: Activity of immobilized UPO against plasma treatment time [min] (40 µL of 1 µM immobilized protein solution; 2 mm distance, 13.5 kV, 300 Hz).

The effect of direct plasma treatment time [min] with a distance of 2 mm on the activity of immobilized UPO (40 µL of 1 µM immobilized protein solution, over 60 min) is demonstrated in FIG. 16. Activity assay parameters: 10 nM UPO; 2.5 mM ABTS in 50 mM sodium acetate buffer, pH 5.5; 1 mM H$_2$O$_2$ while constant shaking at 1400 rpm.

Figure 17:
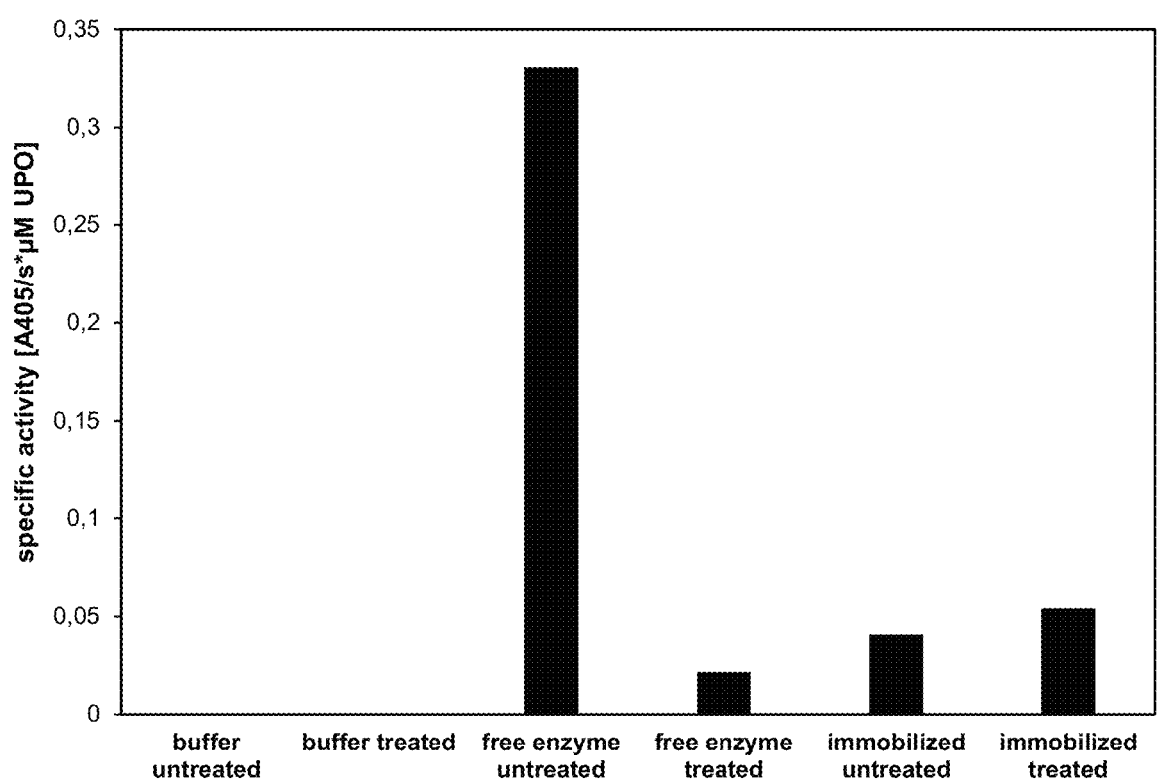
FIG. 17: Specific enzyme activity [A405/s*µM UPO] at varying experimental conditions after 5 min treatment time (40 µL of 1 µM protein solution; 2 mm distance, 13.5 kV, 300 Hz).

The effect of enzyme immobilization and/or direct plasma treatment in comparison to free enzyme and/or samples without direct plasma treatment on the specific enzyme activity of UPO is illustrated in FIG. 17. (40 µL of 1 µM protein solution; 2 mm distance, 5 min treatment time).

Activity assay parameters: 5 nM UPO; 2.5 mM ABTS in 50 mM sodium acetate buffer, pH 5.5; 1 mM H$_2$O$_2$. Activity was calculated from linear slope in the absorption measurement.

In samples which were directly plasma-treated, the substrate conversion was determined by adding commercially available H$_2$O$_2$ to the sample after direct plasma treatment. The substrate used for the respective assay was added after direct plasma treatment.

The invention claimed is:

1. A method for enzymatically oxidizing or hydroxylating an organic compound, wherein the method comprises:
    treating an aqueous liquid with a plasma device to obtain an aqueous liquid comprising H$_2$O$_2$ to form an enzymatically oxidized or hydroxylated organic compound; wherein the aqueous liquid comprises at least one enzyme, at least one organic compound, and optionally at least one solvent; wherein the at least one solvent is not water; wherein the at least one enzyme is immobilized on a solid support and positioned at a distance from the surface of the aqueous liquid in proximity to the plasma device where the distance ranges from 1 mm to 20 cm; and
    optionally extracting the aqueous liquid to isolate the oxidized or hydroxylated organic compound.

2. The method according to claim 1, wherein the plasma device is discontinuously run.

3. The method according to claim 1, wherein:
    the aqueous liquid is water or an aqueous buffer; or
    the aqueous liquid is an aqueous buffer having a pH value ranging from 4 to 8.

4. The method according to claim 1, wherein the H$_2$O$_2$ concentration of the obtained aqueous liquid ranges from 0.05 to 5 mM.

5. The method according to claim 1, wherein the aqueous liquid is treated with the plasma device for an amount of time ranging from 1 min to 24 hours.

6. The method according to claim 1, wherein the plasma device uses one or more of the following:
    a frequency ranging from 30 to 20,000 Hz;
    a voltage ranging from 0.2 to 25 kV peak-to-peak;
    a power ranging from 1 to 10,000 mW; or
    combinations thereof.

7. The method according to claim 1, wherein the organic compound is selected from unsubstituted or substituted alkanes, alkenes, alkines, cyclic or aromatic hydrocarbons, heterocyclic hydrocarbons, amino acids, proteins, alkaloids, steroids, and terpenes, or mixtures thereof.

8. The method according to claim 1, wherein the aqueous liquid and/or the obtained aqueous liquid further comprise at least one auxiliary substance selected from superoxide dismutase, mannitol, 6-hydroxy-2,5,7,8-tetramethylchroman-2-carboxylic acid, ebselen, uric acid, molecular chaperones, peroxynitrite, HOC, nitric acid, and combinations thereof.

9. The method according to claim 8, wherein the at least one auxiliary substance is superoxide dismutase.

10. The method according to claim 1, wherein the at least one enzyme is selected from oxidases, monooxygenases, peroxidases, peroxygenases, or combinations thereof.

11. The method according to claim 1, wherein the plasma device is an atmospheric pressure plasma device.

* * * * *